(12) United States Patent
Forsell

(10) Patent No.: US 12,076,248 B2
(45) Date of Patent: *Sep. 3, 2024

(54) HIP JOINT DEVICE AND METHOD

(71) Applicant: Peter Forsell, Lund (SE)

(72) Inventor: Peter Forsell, Lund (SE)

(*) Notice: Subject to any disclaimer, the term of this patent is extended or adjusted under 35 U.S.C. 154(b) by 93 days.

This patent is subject to a terminal disclaimer.

(21) Appl. No.: 17/389,644

(22) Filed: Jul. 30, 2021

(65) Prior Publication Data

US 2022/0087825 A1    Mar. 24, 2022

Related U.S. Application Data

(63) Continuation of application No. 13/382,643, filed as application No. PCT/SE2010/050803 on Jul. 12, 2010, now Pat. No. 11,103,355.

(Continued)

(30) Foreign Application Priority Data

| | | |
|---|---|---|
| Jul. 10, 2009 | (SE) | 0900957-2 |
| Jul. 10, 2009 | (SE) | 0900958-0 |
| Jul. 10, 2009 | (SE) | 0900959-8 |
| Jul. 10, 2009 | (SE) | 0900960-6 |
| Jul. 10, 2009 | (SE) | 0900962-2 |
| Jul. 10, 2009 | (SE) | 0900963-0 |
| Jul. 10, 2009 | (SE) | 0900965-5 |
| Jul. 10, 2009 | (SE) | 0900966-3 |

(Continued)

(51) Int. Cl.
*A61F 2/32* (2006.01)
*A61B 17/16* (2006.01)
(Continued)

(52) U.S. Cl.
CPC ........ *A61F 2/3607* (2013.01); *A61B 17/1637* (2013.01); *A61F 2/32* (2013.01);
(Continued)

(58) Field of Classification Search
CPC ........ A61F 2/36; A61F 2/3601; A61F 2/3607; A61F 2/3609; A61F 2/34; A61F 2/32;
(Continued)

(56) References Cited

U.S. PATENT DOCUMENTS 3,896,504 A * 7/1975 Fischer ............... A61F 2/32
  606/313
2004/0220673 A1 * 11/2004 Pria ............... A61F 2/4081
  623/19.12

* cited by examiner

*Primary Examiner* — Dinah Baria

(57) ABSTRACT

A medical device for implantation in a hip joint of a human patient is provided. The natural hip joint having a ball shaped caput femur as the proximal part of the femoral bone with a convex hip joint surface towards the centre of the hip joint and a bowl shaped acetabulum as part of the pelvic bone with a concave hip joint surface towards the centre of the hip joint. The caput femur has a centrally placed longitudinal extension, extending through the center of the caput and collum femur, aligned with the collum femur, defined as the caput and collum femur center axis. The medical device comprising; an artificial acetabulum, comprising a concave surface towards the centre of the hip joint. The artificial concave acetabulum is adapted to, when implanted, be fixated to the femoral bone of the human patient, and be in movable connection with an artificial caput femur fixated to the pelvic bone of the patient.

20 Claims, 21 Drawing Sheets

Related U.S. Application Data

(60) Provisional application No. 61/229,738, filed on Jul. 30, 2009, provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(30) Foreign Application Priority Data

| Jul. 10, 2009 | (SE) | 0900968-9 |
|---|---|---|
| Jul. 10, 2009 | (SE) | 0900969-7 |
| Jul. 10, 2009 | (SE) | 0900970-5 |
| Jul. 10, 2009 | (SE) | 0900972-1 |
| Jul. 10, 2009 | (SE) | 0900973-9 |
| Jul. 10, 2009 | (SE) | 0900974-7 |
| Jul. 10, 2009 | (SE) | 0900976-2 |
| Jul. 10, 2009 | (SE) | 0900978-8 |
| Jul. 10, 2009 | (SE) | 0900981-2 |

(51) Int. Cl.

| *A61F 2/34* | (2006.01) |
|---|---|
| *A61F 2/36* | (2006.01) |
| *A61B 17/74* | (2006.01) |
| *A61B 17/86* | (2006.01) |
| *A61F 2/30* | (2006.01) |
| *A61F 2/46* | (2006.01) |

(52) U.S. Cl.
CPC ............... *A61F 2/34* (2013.01); *A61F 2/36* (2013.01); *A61F 2/3601* (2013.01); *A61F 2/3603* (2013.01); *A61F 2/3609* (2013.01); A61B 17/1664 (2013.01); A61B 17/74 (2013.01); A61B 17/86 (2013.01); A61F 2002/30471 (2013.01); A61F 2002/30507 (2013.01); A61F 2002/30558 (2013.01); A61F 2002/30563 (2013.01); A61F 2002/30565 (2013.01); A61F 2002/30579 (2013.01); A61F 2002/30878 (2013.01); A61F 2002/30886 (2013.01); A61F 2002/3241 (2013.01); A61F 2002/3483 (2013.01); A61F 2002/3615 (2013.01); A61F 2002/3631 (2013.01); A61F 2002/365 (2013.01); A61F 2002/4631 (2013.01); A61F 2002/4635 (2013.01); A61F 2002/4677 (2013.01); A61F 2240/002 (2013.01)

(58) Field of Classification Search
CPC ...... A61F 2002/3615; A61F 2002/3631; A61F 2002/3483; A61F 2002/365
See application file for complete search history.

A - A

B - B

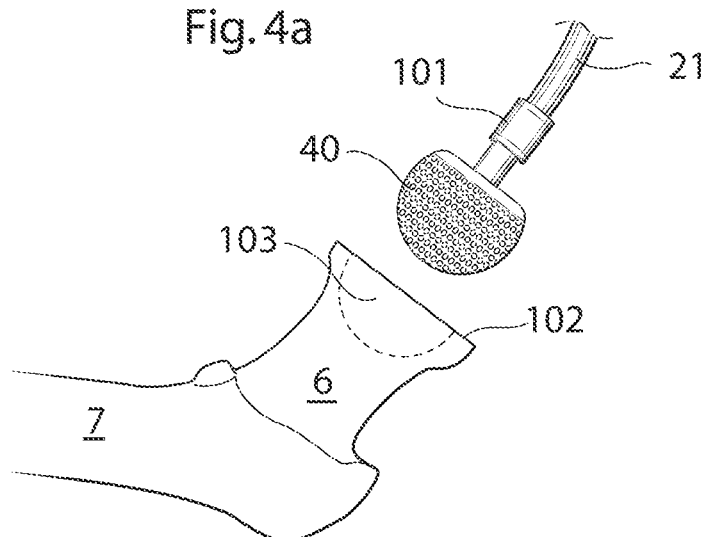
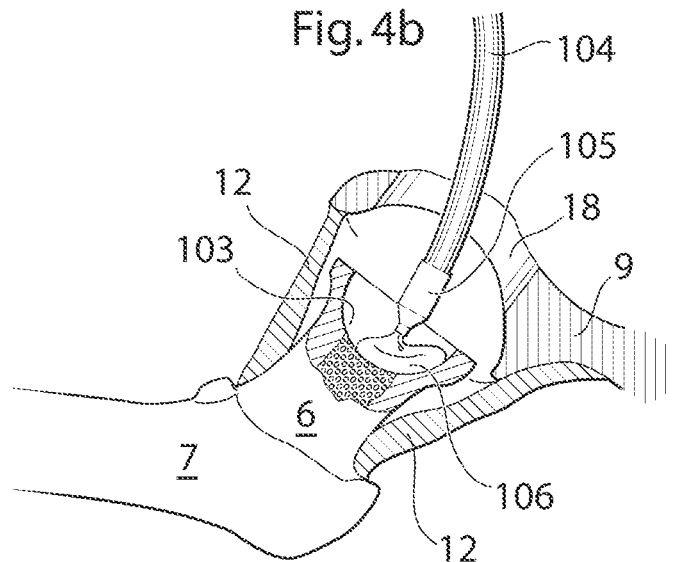
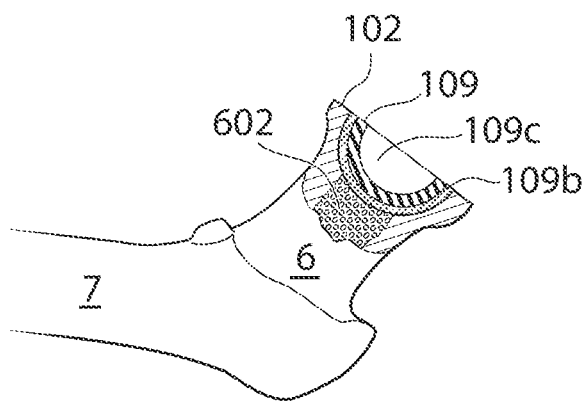

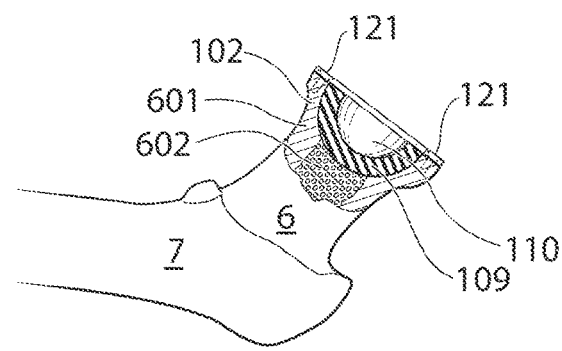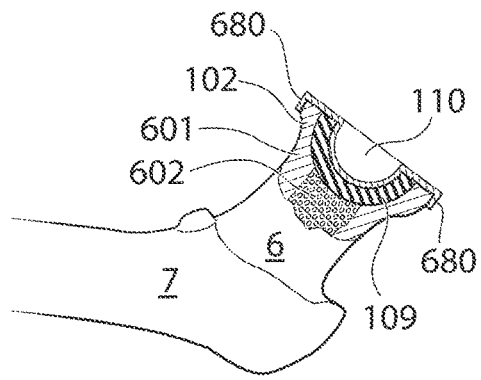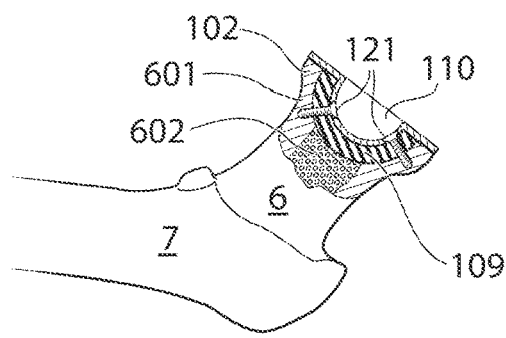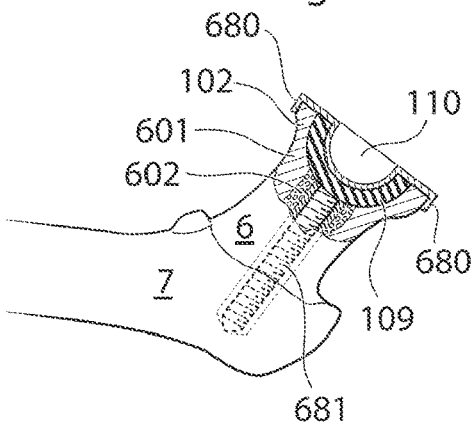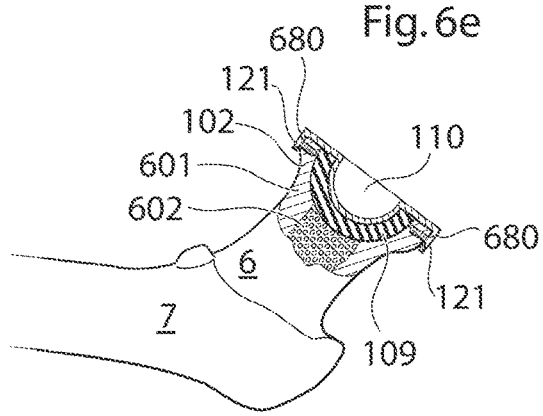

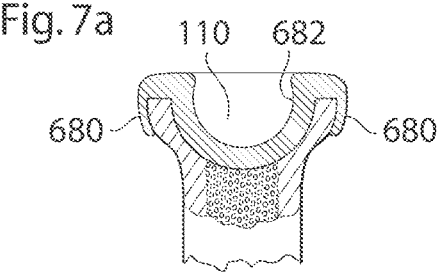
Fig. 7a
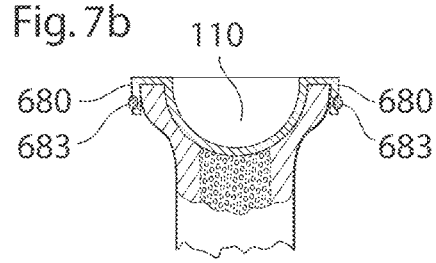
Fig. 7b
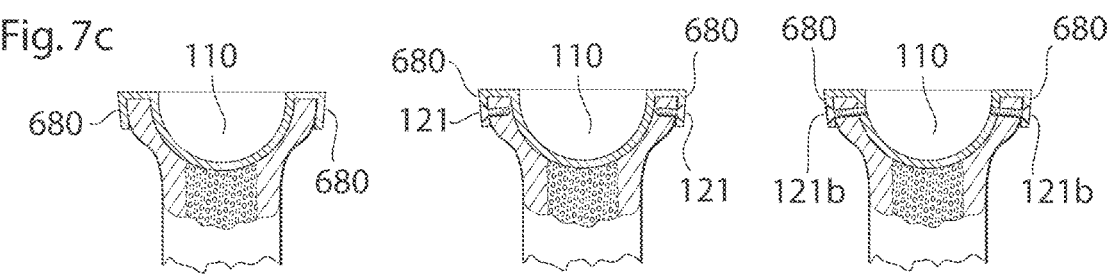
Fig. 7c
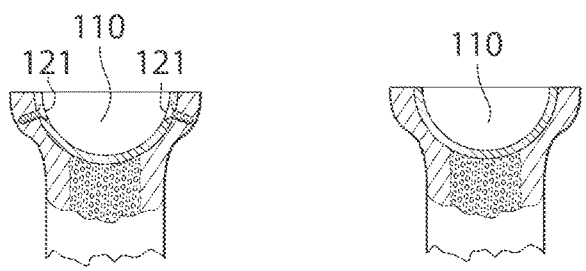
Fig. 7d
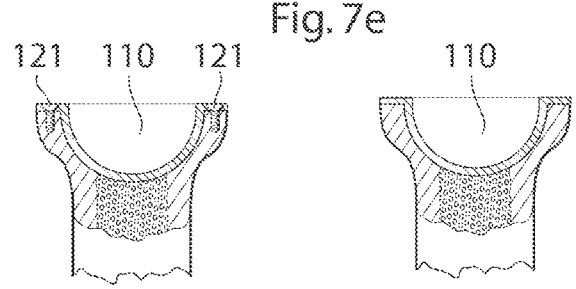
Fig. 7e
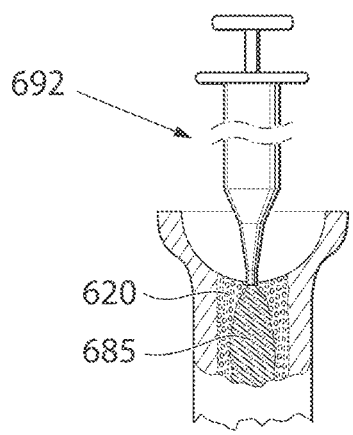
Fig. 7f
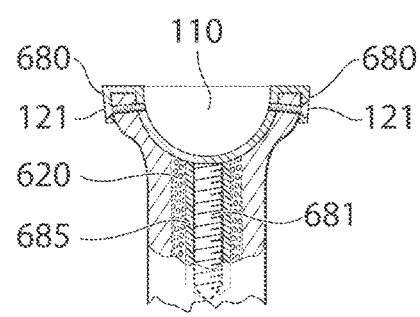

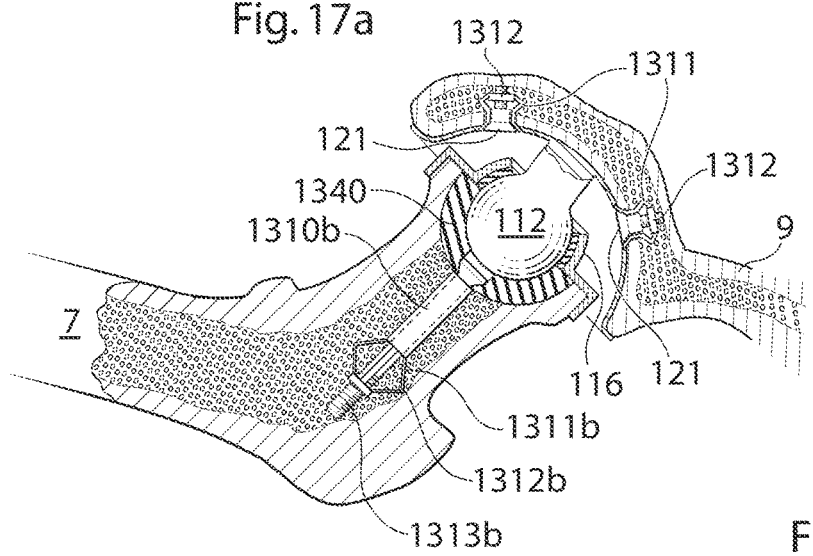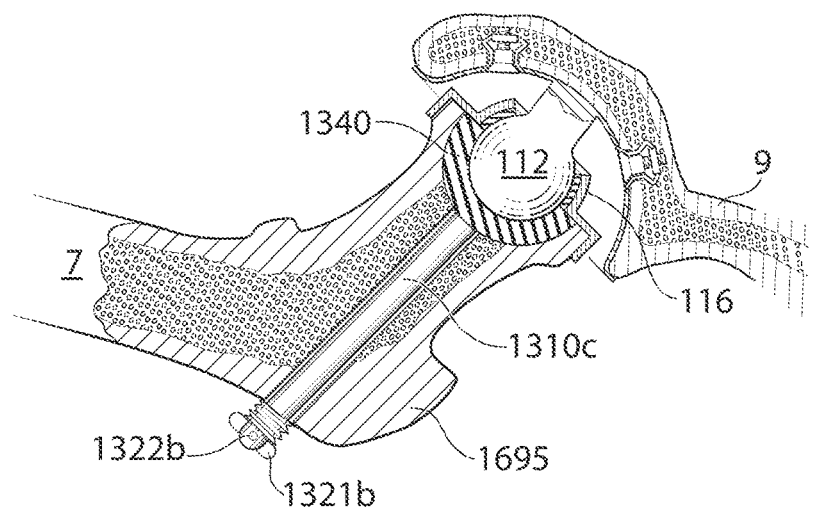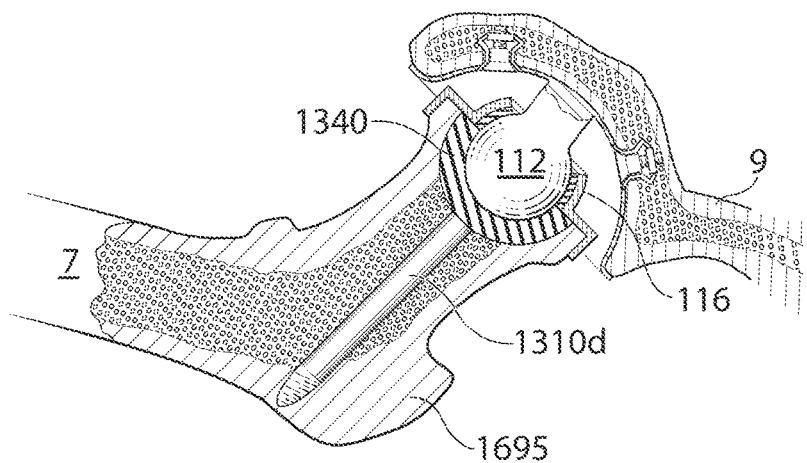

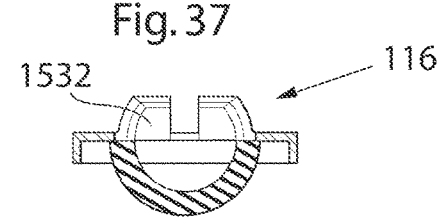
Fig. 37
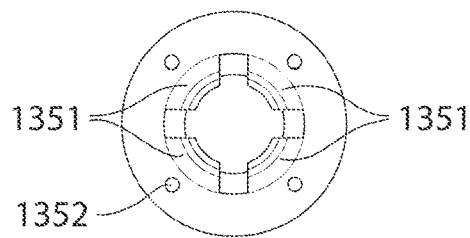
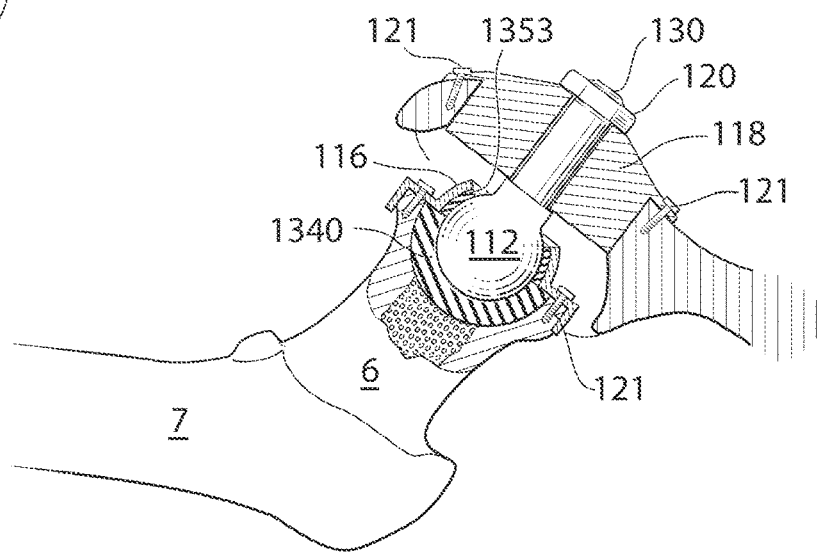
Fig. 38
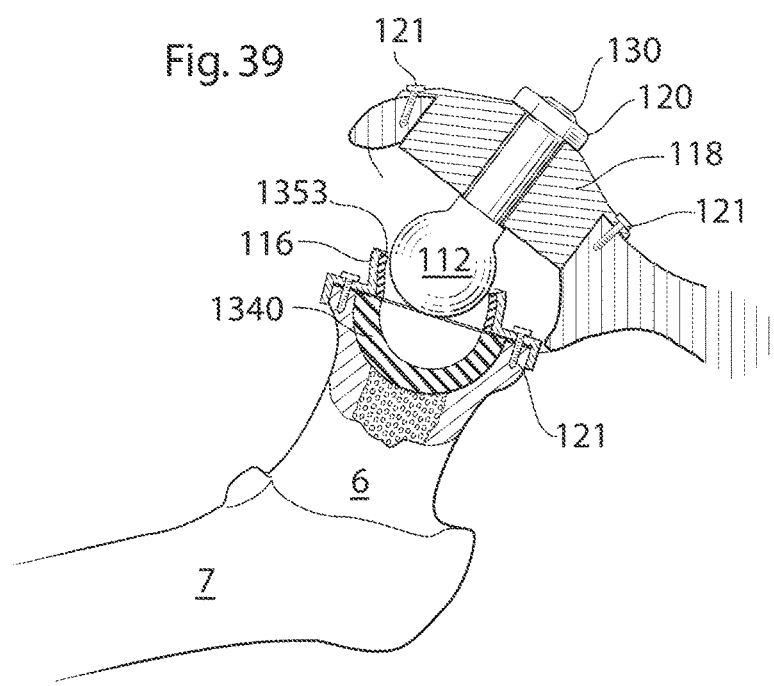
Fig. 39

HIP JOINT DEVICE AND METHOD

This application is a continuation of U.S. patent application Ser. No. 13/382,643 filed Jan. 6, 2012, which is the U.S. national phase of International Application No. PCT/SE2010/050803, filed 12 Jul. 2010, which designated the U.S. and claims the benefit of U.S. Provisional No. 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application No. 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 090097 4-7 filed 10 Jul. 2009; 0900976-2 filed 10 Jul. 2009 and 0900978-8 filed 10 Jul. 2009, the entire contents of each of which are hereby incorporated by reference.

FIELD OF INVENTION

The present invention relates generally to a medical device for implantation in a hip joint, and a method of providing said medical device.

BACKGROUND ART

The hip joint is a synovial joint, joining the pelvis to the proximal portion of the femoral bone. Synovial joints are the most common types of joints in mammals, and are typical of nearly all limb joints. The contacting surfaces of said the pelvic, the acetabulum, and the contacting surface of the femoral bone, the caput femur, are smooth and rounded, and covered by articular cartilage. A synovial membrane, encapsulates the joint, forming a hip joint cavity, which contains synovial fluid. Outside the synovial membrane is a fibrous capsule and ligaments, forming an articular capsule.

There are both natural and pathological processes leading to deteriorated joint function. With age and wear, the articular cartilage becomes less effective as a shock absorber and a lubricated surface. Different degenerative joint diseases, such as arthritis, osteoartrithis, or osteoarthrosis, accelerate the deterioration.

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through an incision in the hip and upper thigh and through Fascia Lata and the lateral muscles of the thigh. To get access to the joint, the supporting Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The complications after hip joint surgery includes dislocation of the hip joint and loosening of the prosthesis from its fixation in the femoral bone. The loosening and/or dislocation of the prosthesis could be induced by an abnormal strain being placed on the hip joint from e.g. the patient falling or making a rapid movement of the hip, or by a bodily macrophage reaction.

SUMMARY

A medical device for implantation in a hip joint of a human patient is provided. The natural hip joint having a ball shaped caput femur as the proximal part of the femoral bone with a convex hip joint surface towards the centre of the hip joint and a bowl shaped acetabulum as part of the pelvic bone with a concave hip joint surface towards the centre of the hip joint. The caput femur has a centrally placed longitudinal extension, extending through the center of the caput and collum femur, aligned with the collum femur, defined as the caput and collum femur center axis. The medical device comprising; an artificial acetabulum, comprising a concave surface towards the centre of the hip joint. The artificial concave acetabulum is adapted to, when implanted, be fixated to the femoral bone of the human patient, and be in movable connection with an artificial caput femur fixated to the pelvic bone of the patient.

According to one embodiment the medical device comprises a fixating portion adapted to be; stabilized by the cortical bone of the caput femur, from the inside of the caput femur or stabilized by the cortical bone of the collum femur from the inside of the collum femur, when at least one of the caput and collum femur has been surgically modified and opened.

According to one embodiment the medical device comprises a fixating portion adapted to be; stabilized by the cortical bone of the caput femur, substantially from the proximal side of the cortical bone of the caput femur, or stabilized by the cortical bone of the collum femur substantially from the proximal side of the cortical bone of collum femur, when at least one of said caput and collum femur has been surgically modified having a cut through corticalis edge of the caput or collum femur supporting said fixating portion.

According to one embodiment, the medical device comprises a fixating portion adapted to be; stabilized by the cortical bone of the caput femur, from the outside of the caput femur or stabilized by the cortical bone of the collum femur, from the outside of the collum femur.

According to yet another embodiment, the medical device comprises a fixating portion adapted to be; stabilized by the cortical bone of the caput femur or collum femur, substantially from the proximal side of a surgically modified cortical bone and from the inside of the caput femur or the collum femur, when at least one of the caput and collum femur has been surgically modified and opened.

According to yet another embodiment the medical device comprises a fixating portion adapted to be; stabilized by the cortical bone of the caput or collum femur, substantially from the proximal side of a surgically modified cortical bone and from the outside of the caput or collum femur.

According to yet another embodiment the medical device comprises a fixating portion adapted to be stabilized by the cortical bone of the caput or collum femur, from the inside of caput or collum femur and from the outside of the caput or collum femur.

The fixating portion could comprise at least one cavity adapted to receive a mechanical fixation element.

The medical device could in any of the embodiments herein further comprise a mechanical fixation element adapted to be placed in at least one cavity of the medical device and inside of the cortical bone of the caput or collum femur, when the medical device is implanted.

According to one embodiment, the medical device comprises a mechanical fixation element adapted to be placed inside of the cortical bone of the caput or collum femur from the inside of the caput femur and/or from the outside of the caput femur.

The mechanical fixation element could in any of the embodiments, be adapted to be placed inside of the cortical bone of the caput or collum femur, substantially from the proximal side of the caput femur.

In any of the embodiments, the medical device could comprise a recess adapted to receive a portion of the femoral bone.

According to one embodiment, the mechanical fixating element could be adapted to be placed partially inside of a first portion of said medical device, on a first side of said recess, partially inside of the portion of the femoral bone placed in said recess, and partially inside of a second portion of said medical device, on a second opposite side of said recess, for restraining the portion of the femoral bone in said recess.

According to another embodiment, the medical device further comprises an elongated element adapted to be placed in the collum femur from the proximal side thereof to stabilize the medical device.

According to yet another embodiment, the medical device comprises an elongated element comprising a threaded portion. The threaded portion could be adapted to engage at least one of: the cortical bone of the collum femur, the cancellous bone of the collum femur, and an artificial material injected into the collum femur.

According to another embodiment, the elongated element could comprise an anchoring portion, and said anchoring portion could be adapted to engage at least one of: the cortical bone of the collum femur, the cancellous bone of the collum femur, and an artificial material injected into the collum femur.

According to yet another embodiment the anchoring portion could have a first and second state, and said anchoring portion could be adapted to, in said second state, further engage at least one of: the cortical bone of the collum femur, the cancellous bone of the collum femur, and an artificial material injected into the collum femur, for further fixating said medical device to the femoral bone.

According to yet another embodiment, the medical device comprises a fixating portion further comprising at least one groove adapted to stabilize a loop-shaped fixating element along at least one portion thereof, when said medical device is implanted.

The loop-shaped fixating element could be adapted to further stabilize the medical device to the femoral bone. The loop shaped fixating element is could be elastic or the medical device could comprise an elastic portion which could be adapted to clasp a portion of the femoral bone and thereby fixate the medical device to the femoral bone.

According to yet another embodiment, the medical device is adapted to pass beyond the equator of the artificial caput femur placed in the medical device when implanted, thereby clasping the artificial caput femur.

According to yet another embodiment the medical device further comprises a locking member adapted to lock an artificial caput femur in the medical device.

According to yet another embodiment, the locking member could comprise an elastic portion which could be an elastic band adapted to encircle the artificial caput femur.

According to yet another embodiment, the medical device has a first and second state, and the medical device could be adapted to, in said first state, fixate the artificial caput femur to the medical device, and in said second state, release the artificial caput femur from the medical device. The medical device could be adapted to change from said first state to said second state when a predetermined strain is placed on said medical device.

The locking member of the medical device could comprise an elastic or flexible portion, and the locking member could be adapted to change the medical device from the first to the second state using the elasticity or flexibility of the elastic or flexible portion of the locking member.

According to yet another embodiment the medical device comprises a surface adapted to be placed in contact with the cortical or cancellous bone of the femoral bone, when implanted, and said surface could be adapted to adhere to the cortical or cancellous bone using an adhesive.

According to yet another embodiment, the medical device comprises a surface adapted to promote in-growth of bone tissue for fixating said medical device to the femoral bone, by means of for example a porous micro or nano structure.

The fixating portion, adapted to stabilize the medical device to the femoral bone, could in any of the embodiments herein be elastic or flexible.

In some embodiments, the medical device comprises an elastic or flexible portion, which could be adapted to clasp a portion of the femoral bone from the outside of the cortical bone of caput or collum femur and thereby fixate the medical device to the femoral bone.

The fixating portion adapted to clasp at least one portion of the femoral bone from the outside of the cortical bone of caput or collum femur and thereby at least partly fixate the medical device to the femoral bone.

In some embodiments, the fixating portion is adapted to pass proximal beyond the equator of caput femur aligned with the caput and collum center axis, when implanted and engaging a surgically modified caput femur, thereby clasping the surgically modified caput femur to stabilize the medical implant.

The surgically modified caput or collum femur comprises a most proximal portion. The fixating portion could be adapted to pass beyond the most proximal portion, on the outside thereof, thus partially be placed more distal than the most proximal portion of the surgically modified caput or collum femur.

According to yet another embodiment a portion of the caput or collum femur is placed at a largest distance from the caput and collum femur center axis, and wherein a portion of said fixating portion is adapted to be placed at a distance from the caput and collum center axis, being shorter than the largest distance from the caput and collum femur center axis to the caput or collum femur.

The fixating portion could according to one embodiment, be adapted to clasp a portion of the caput or collum femur, said fixating portion thereby assisting in the fixation of the medical device to the caput or collum femur. This could be done by the closest distance from said fixating portion to said caput or collum center axis being shorter than the distance between said center axis and the equator of the caput femur.

According to another embodiment, the medical device further comprises an elastic layer adapted to absorb chocks from the femoral bone. The elastic layer could be placed between the femoral bone and the medical device, when said medical device is implanted, the elastic layer could be an elastic polymer layer.

The elastic polymer layer could for example be an elastic polymer layer selected from a group consisting of: polyurethane, silicone, a combination of polyurethane and silicone, parylene coated silicone, parylene coated polyurethane, and a parylene coated combination of polyurethane and silicone.

A method of replacing a natural hip joint with an artificial hip joint is further provided. The method comprising the steps of: exposing the caput femur, opening the caput femur, thereby exposing the cortical and cancellous bone of the caput femur, placing a medical device comprises an artificial concave acetabulum surface in the caput femur and fixating the medical device to the caput femur or collum femur.

According to one embodiment, the step of fixating the medical device to the caput or collum femur, comprises the step of fixating the medical device to the cortical bone from the inside of the caput or collum femur and/or from the outside of the caput or collum femur and/or from the proximal side of the caput or collum femur.

According to yet another embodiment, the medical device comprises an elastic portion, and the step of fixating the medical device could further comprise the step of fixating the medical device to the caput femur by the medical device clasping the caput femur using the elastic portion.

According to one embodiment, the medical device comprises an elongated member, and the step of fixating the medical device comprises placing the elongated member in the collum femur, substantially aligned with the caput and collum femur center axis, the elongated member engaging at least one of: the cancellous bone of the collum femur, the cortical bone of the collum femur and an artificial material placed inside of the collum femur.

The elongated member could comprise a threaded portion, and the step of placing the elongated member in the collum femur could comprise the step of screwing the elongated into the collum femur.

According to yet another embodiment, the elongated member could comprise an anchoring portion, and the step of placing the elongated member in the collum femur could comprise the step of placing the anchoring portion such that the anchoring portion engages at least one of: the cancellous bone of the collum femur, the cortical bone of the collum femur and an artificial material placed inside of the collum femur.

According to another embodiment, the anchoring portion can be placed in a first and second state, and said anchoring portion could be adapted to, in the second state, further engage at least one of: the cancellous bone of the collum femur, the cortical bone of the collum femur and an artificial material placed inside of the collum femur, for further stabilizing the medical device.

In yet another embodiment, the medical device further comprises applying an adhesive to a surface of the inside of the caput or collum femur and placing the medical device in contact with said adhesive, such that said adhesive adheres to the medical device.

According to yet another embodiment, the step of fixating the medical device comprises the step of fixating the medical device using a mechanical fixation element adapted to engage the cortical bone of the caput or collum femur.

In yet another embodiment, the step of fixating the medical device comprises the step of fixating the medical device using a mechanical fixation element adapted to engage the cortical bone of the caput or collum femur.

In yet another embodiment, the step of fixating the medical device could comprise the step of placing a mechanical fixation element in connection with the medical device, clamping the medical device, and thus fixating the medical device to the caput femur.

In other embodiments, the step of placing the mechanical fixation element comprises the step of placing a loop shaped mechanical fixation element surrounding the medical device and caput femur.

In other embodiments, step of fixating the medical device to the caput or collum femur, comprises fixating the medical device to the cortical bone of caput or collum femur from at least one of; the outside, the inside and a proximal cut caput or collum femur and operating the device to adjust the fixation to clamp the cortical bone of the caput or collum femur.

According to one embodiment, the fixating portion is adapted to be operable to adjust the stabilization of the medical device towards the cortical bone of the caput or collum femur, from at least one of; the inside of caput or collum femur, the outside of the caput or collum femur and a cut proximal side of caput or collum femur.

Please note that any embodiment or part of embodiment as well as any method or part of method could be combined in any way. All examples herein should be seen as part of the general description and therefore possible to combine in any way in general terms.

BRIEF DESCRIPTION OF DRAWINGS

The invention is now described, by way of example, with reference to the accompanying drawings, in which:

FIGS. 4a-4b shows the reaming of the collum and caput femur,

FIG. 5 shows the collum and caput femur when a medical device gas been fixated,

FIGS. 6a-6e shows the reaming of the acetabulum,

FIGS. 7a-7f shows the injecting of an adhesive in the acetabulum, FIGS. 17a-17c shows the hip joint in section when an injecting member injects a fluid through a hole in the pelvic bone.

FIG. 37 shows an embodiment of a locking member 116, wherein the locking member comprises a surface adapted to be in contact with the artificial convex hip joint surface FIG. 38 shows the hip joint in section when a two state locking member locks the artificial caput femur in the artificial acetabulum.

FIG. 39 shows the hip joint in section according to the embodiment of FIG. 38, but when the two state locking member is in its second state.

DETAILED DESCRIPTION

Figure 1A:
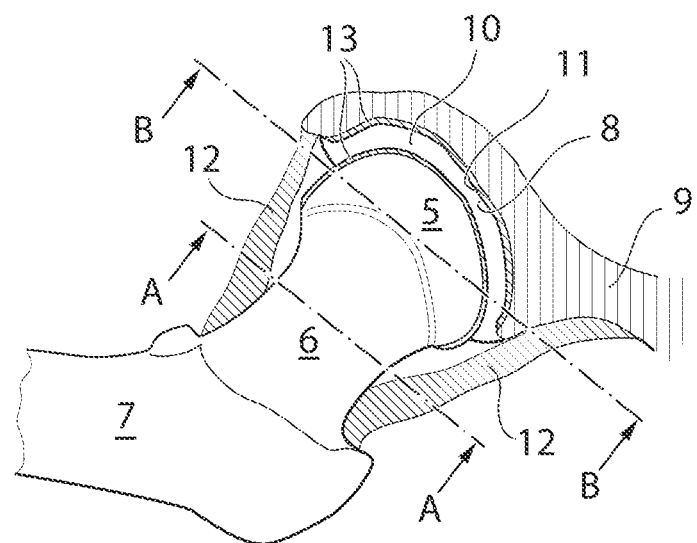
FIG. 1a shows the hip joint in section.

In the following a detailed description of preferred embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical device or prosthesis is the position in which the hip joint can perform functional hip movements. The final position is to be understood as a functional position in which the medical device needs no further position change.

Arthroscopy is to be understood as key hole surgery performed in a joint, since the arthroscopic procedure could be performed in the abdomen of the patient some of the steps of this arthroscopic procedure is more laparoscopic, however for the purpose of this invention the two terms arthroscopy and laparoscopy is used synonymously and for the purpose of this invention the main purpose of these methods are is that they are minimally invasive.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

FIG. 1a shows the hip joint of a human patient in section. The hip joint comprises a caput femur 5 placed at the very top of collum femur 6 which is the top part of the femoral bone 7. The caput femur is in connection with the acetabulum 8, which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 1B:
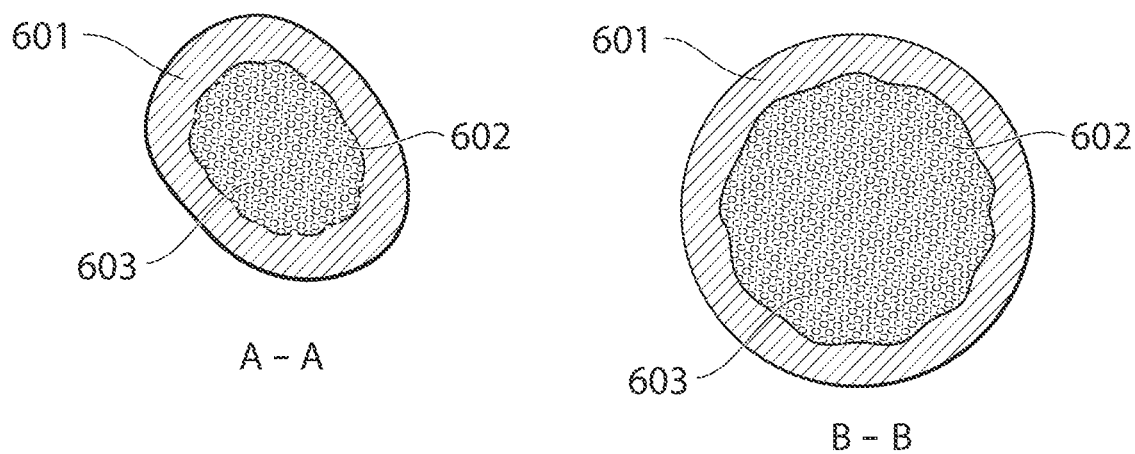
FIG. 1b shows the collum femur in section.

FIG. 1b shows a section A—A of the collum femur, as shown in FIG. 1. The section A—A shows the collum femur comprising cortical bone 601, the outer more sclerotic bone, and cancellous bone 602, the inner porous bone located in the bone marrow 603. Further, FIG. 1b shows a section B—B of the caput femur, perpendicular to the length axis of the collum 6 and caput 5 femur.

Figure 2:
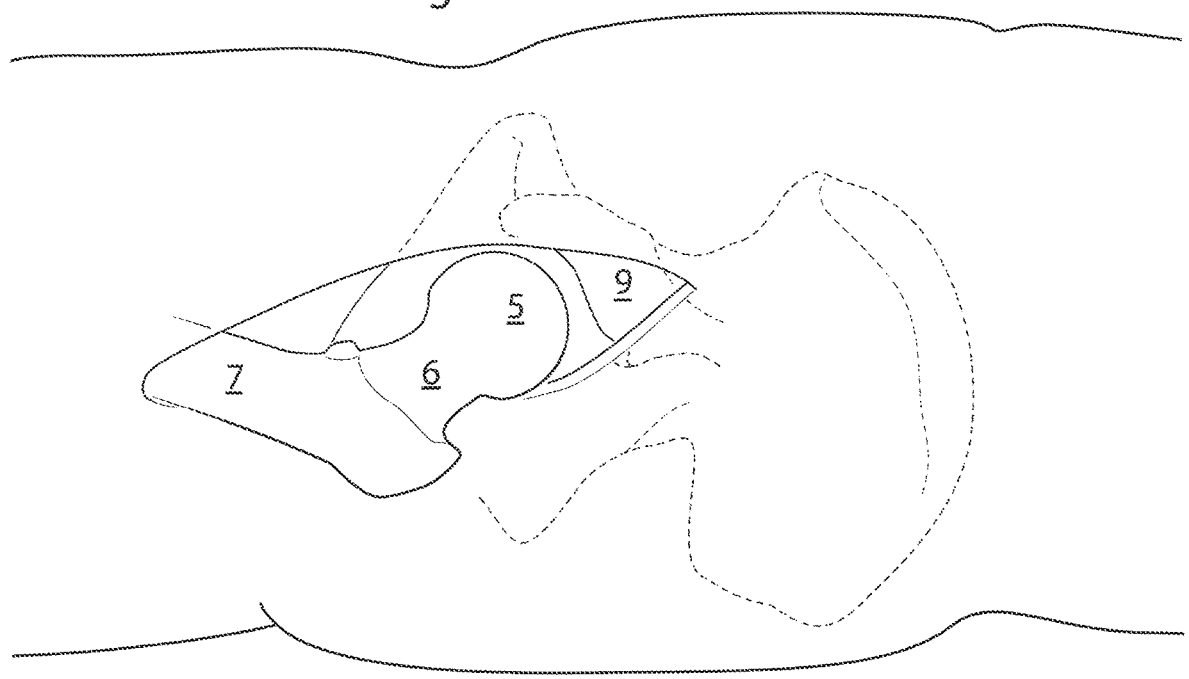
FIG. 2 shows the exposing of the caput femur through an incision in the thigh.

FIG. 2 shows a lateral view of a human patient when an incision in the thigh region has been made. The femoral bone 7 comprising the collum femur 6 and the caput femur 5 has been dislocated from its usual position in the hip joint, in connection with the acetabulum, which is a part of the pelvic bone 9, the caput femur 5 being a part of the hip joint normally being covered by the hip joint capsule.

Figure 3:
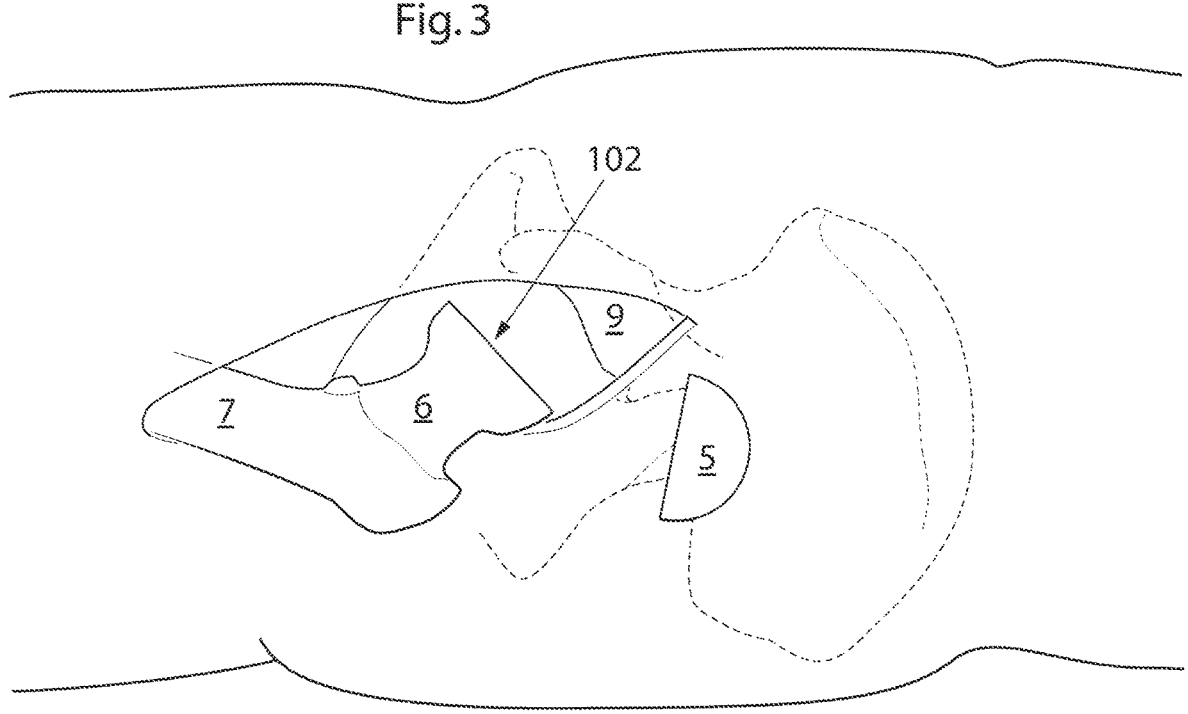
FIG. 3 shows the step of removing a proximal part of the caput femur.

FIG. 3 shows the proximal part of the caput femur 5 being removed e.g. by means of a bone saw. A surface of a section 102 is thus created perpendicularly to a length axis of the collum femur 6

FIG. 4a shows the reaming of the collum femur 6 and caput femur 5 using a reamer 40 connecting to an elongated member 21 by a connecting section 101. The reamer 40 creating a hemi-spherical cavity, having a concave surface 103, centrally placed in the caput 5 and collum femur 6.

FIG. 4b shows the step of applying an adhesive 106 to the created hemi-spherical cavity in the femoral bone using an injecting member 104 having an injecting nozzle 105. In the embodiment shown in FIG. 4b the injecting member is inserted into an area of the hip joint through a hole 18 in the pelvic bone 9, however it is equally conceivable that the injecting member is inserted through the hip joint capsule 12 or the femoral bone 7.

FIG. 5 shows the femoral bone 7 when a medical device 109 having a concave contacting surface has been provided to the hemi-spherical cavity, centrally placed in the caput 5 and collum femur. An elastic layer 109b adapted to absorb shocks from the femoral bone has been placed between the surface 109c adapted to be in contact with the artificial caput femur surface, and the femoral bone 7, 6. The elastic layer 109b could be an elastic polymer layer, such as a polyurethane or silicone layer. Having a layer absorbing shocks in the hip joint reduces the risk of fastening elements in contact with bone being affected by strains such that the fastening elements are loosened from their respective fastening positions, it also increases the comfort for the patient.

FIG. 6a shows the femoral bone 7 when a medical device having a concave contacting surface 110 has been provided to the hemi-spherical cavity, centrally placed in the caput 5 and collum femur. The medical device has been fixated to the femoral bone 7 using screws 121 placed aligned with the caput and collum femur center axis and entering the cortical bone of the caput femur.

FIG. 6b shows the femoral bone 7 when a medical device having a concave contacting surface 110 has been provided to the hemi-spherical cavity, centrally placed in the caput 5 and collum femur. The medical device comprises fixating portions 680 extending on the outside of the surface of a section 102 of the surgically cut caput femur, comprising cortical bone in the periphery thereof, thereby stabilizing the medical device with the artificial concave acetabulum surface 110 in the surgically cut caput femur.

FIG. 6c shows an alternative embodiment, in which the medical device has been fixated to the surgically cut caput femur using screws 121 entering the cortical bone 601 of the caput femur.

FIG. 6d shows yet another embodiment, in which the medical device is fixated to the femoral bone using fixating portions, in accordance with the embodiment described with reference to FIG. 6b, and an elongated member 681. The elongated member is according to this embodiment a threaded member 681 extending along the collum and caput femur center axis, in the cancellous bone 602 of the collum femur, and entering the cortical bone 601 of the femoral bone, on the inside thereof, in the area of the greater trochanter. The threaded elongated member 681 creates an axial force when pulled pressing the medical device towards the surface of a section 102 of the surgically cut caput femur, thereby stabilizing and fixating the medical device in the concave cavity created in the caput femur.

FIG. 6e shows yet an alternative embodiment of the medical device in which the fixating portions 680 are additionally fixated using screws 121 placed from the outside of the surgically cut caput femur, perpendicularly to the collum and caput femur center axis.

FIG. 7a shows the medical device in an embodiment in which the fixating portions 680 extends beyond the greatest circumference of the surgically cut caput femur and thereby clasps the medical device to the surgically cut caput femur, fixating the medical device thereon. The concave contacting surface 110 is also adapted to travel beyond the equator of an artificial caput femur which is placed in the artificial acetabulum when mounted into a functioning artificial hip joint, and clasping the artificial caput femur when mounted therein.

FIG. 7b shows yet another embodiment where the medical device is additionally fixated using a fixating band 683 encircling the fixating portions of the medical device and thereby further clasping the medical device to the surgically cut caput femur.

FIG. 7c shows three different embodiment of medical devices comprising fixating portions 680 which are slightly tilted towards the collum and caput femur center axis, thereby clasping a portion of the surgically cut caput femur for fixating the medical device to the surgically cut caput femur. The three different embodiments shown is first, without screws 121, second, with screws entering the cortical bone, and third, with screws penetrating the cortical bone and entering the medical device on the inside of the concave cavity, which enables the screws to squeeze a portion of the cortical bone for tight fixation of the medical device.

FIG. 7d shows two embodiments in which the concave contacting surface 110 only comprises the part placed inside of the concave cavity. The first embodiment shows the acetabulum surface 110 fixated to the concave cavity using screws 121, whereas the second embodiment shows the artificial acetabulum surface fixated without screws, such as using an adhesive.

FIG. 7e shows two embodiments in which the artificial acetabulum surface extends into a portion placed on the surface of a section created when the caput femur is surgically cut. In the first embodiment the medical device is fixated using screws entering the cortical bone, whereas in the second embodiment the artificial contacting surface is fixated without screws, such as using an adhesive.

FIG. 7f describes an embodiment in which the medical device is further fixated using an elongated member 681, fixating portions 680, and screws 121 placed between the fixating portions 680 and the inside of the artificial acetabulum contacting surface 110. The elongated member 681 is according to this embodiment a threaded member 681 and the first fig. discloses the preparation of the cancellous bone 602 with a curing fluid 685, such as bone cement, creating a sturdy base for the fixation of the threaded member 681.

Figure 8:
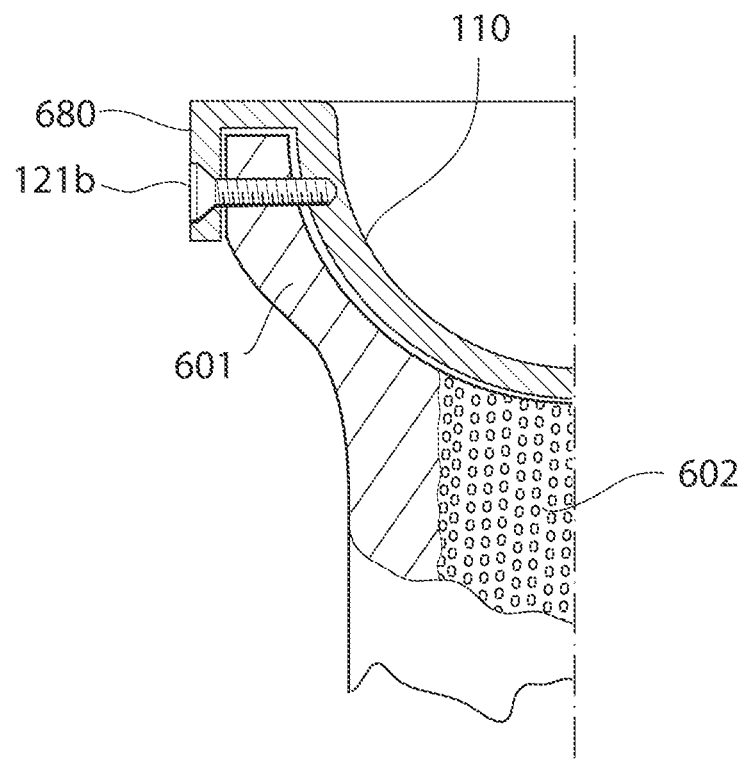
FIG. 8 shows the fixation of a medical device in the acetabulum.

FIG. 8 shows the artificial acetabulum surface 110 in further detail when the artificial acetabulum surface comprises a fixating portion 680 extending on the outside of the cortical bone 601. The fixating portion 680 is further fixated using screws 121 placed from the outside, through a hole in the medical device, penetrating the cortical bone 601 of the surgically cut caput femur and entering the medical device placed in the concave cavity in the caput femur.

Figure 9:
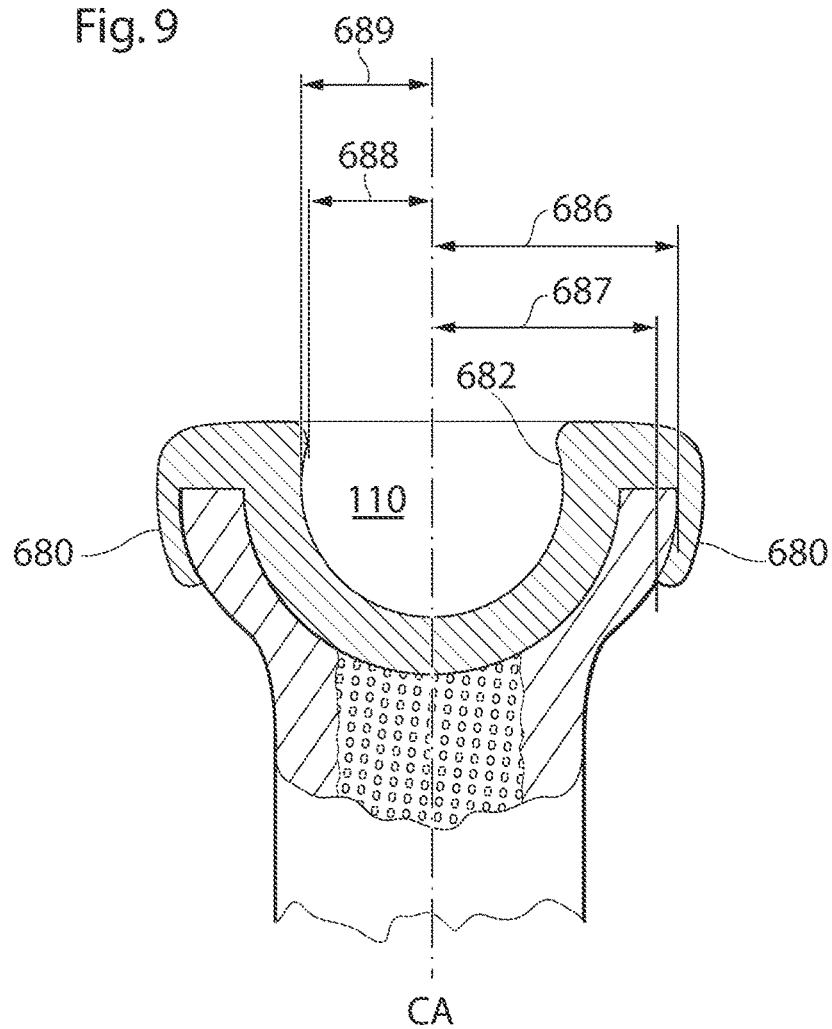
FIG. 9 shows an artificial hip joint, when connected.

FIG. 9 shows a section of the medical device according to the embodiment also described with reference to FIG. 7a, in further detail. The medical device according to the embodiment in FIG. 9 comprises fixating portions 680 which reaches on the outside of the surgically cut caput femur and clasps the cortical bone of the caput femur. The medical device clasps the caput femur since a distance 687, between the collum and caput femur center axis CA and the fixating portion in shorter than a distance 686 between the collum and caput femur center axis CA and a portion of the fixating portion placed more proximally when the medical device is implanted. On the inside of the artificial concave acetabulum surface, the surface extends beyond the equator of the artificial caput femur adapted to be placed therein. An extending portion 682 clasps the artificial caput femur placed in the artificial acetabulum surface 110 since a distance 688, between the collum and caput femur center axis CA and the inside of the artificial acetabulum surface 110 is shorter than a distance 689 between the collum and caput femur center axis CA and a point on the inside of the artificial acetabulum contacting surface 110 being more distal when the medical device is implanted. In other embodiments, the fixating portions 680 could be operable or adjustable for further fixating the medical device to the cortical bone. The fixating portions 680 could be operable for example by means of a screw for tightening the fixating portions 680 to the cortical bone, which could squeeze the cortical bone between the fixating portions 680 and the part of the medical device placed inside of the femoral bone.

Figure 10A:
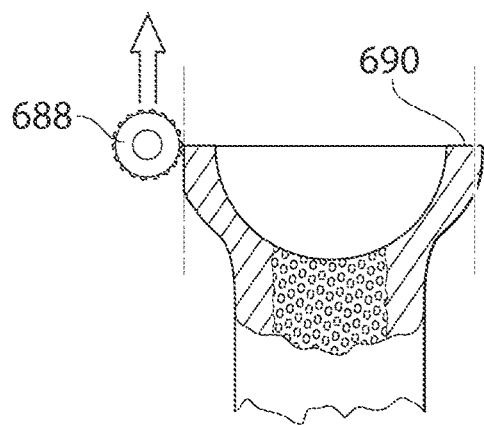
FIGS. 10a-10b shows a medical device when anchored in the femoral bone.

FIG. 10a shows the step of milling the periphery 690 of the cortical bone of the caput femur after the caput femur has been surgically cut, using a milling device 688 adapted therefor. The milling process creates a straighter edge which facilitates the fixation of a medical device on the outside of the caput femur.

Figure 10B:
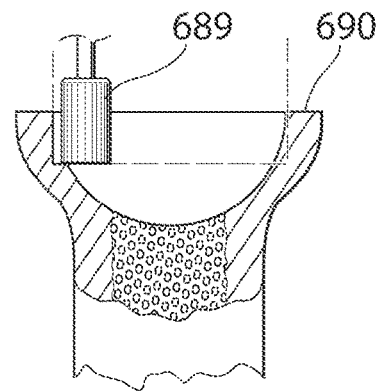

FIG. 10b shows the milling of the inside of the cortical bone of the caput femur after the caput femur has been surgically cut, using a milling device 689 adapted therefor, creating a straighter edge which facilitates the fixation of a medical device on the inside of the caput femur.

Figure 11:
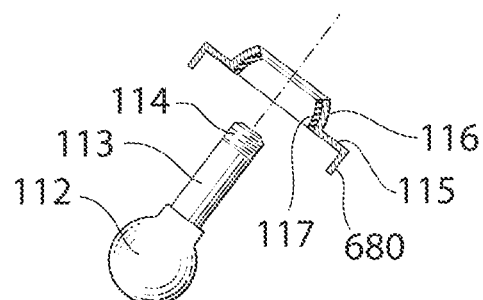
FIG. 11 shows a frontal view of a human patient when incisions have been made in a surgical method.

FIG. 11 shows an artificial convex caput femur surface 112 adapted to be placed in an artificial acetabulum surface according to any of the embodiments herein. After the artificial convex caput femur surface has been placed in the artificial acetabulum surface it is locked using a locking member 116 comprising a surface 117 adapted to be in contact with the artificial convex hip joint surface 112. The locking member 116 further comprises fixating members 115 which are adapted to assist in the fixation of the locking member 116 to the caput femur 5 or collum femur 6, which in turns fixates the artificial convex hip joint surface 112. The fixating members comprises a fixating portion 680 which travels on the outside of the surgically cut caput femur for radially stabilizing and fixating the locking member to the surgically cut caput femur. The artificial convex hip joint surface 112 is fixated to an attachment rod 113 comprising a thread 114.

Figure 12:
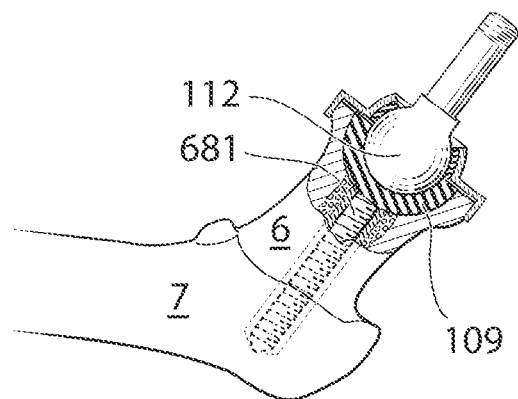
FIG. 12 shows a frontal view of a human patient when incisions have been made in a arthroscopic method.

FIG. 12 shows the artificial convex caput femur surface 112 as disclosed with reference to FIG. 11 when mounted in an artificial acetabulum surface 109 placed in a concave cavity in the femoral bone. The artificial acetabulum surface is according to this embodiment is fixated to the femoral bone using an elongated member 681, here being a threaded member placed aligned with the collum and caput center axis.

Figure 13:
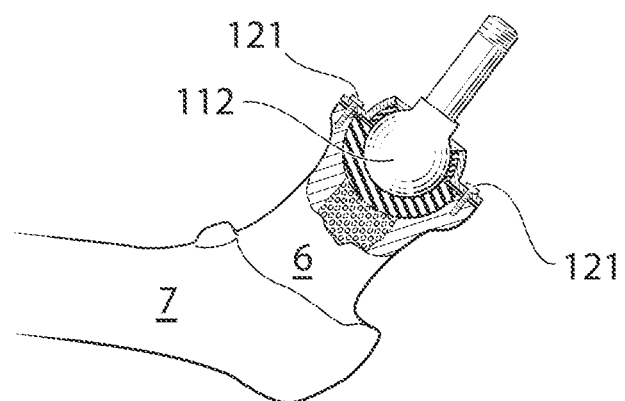
FIG. 13 shows the human patient in section when a medical device for creating a hole in the pelvic bone is inserted.

FIG. 13 shows the artificial convex caput femur surface 112 as disclosed with reference to FIG. 11 when mounted in an artificial acetabulum surface 109 placed in a concave cavity in the femoral bone. The artificial acetabulum surface is according to this embodiment is fixated using screws 121 entering the cortical bone of the surgically cut caput femur.

Figure 14:
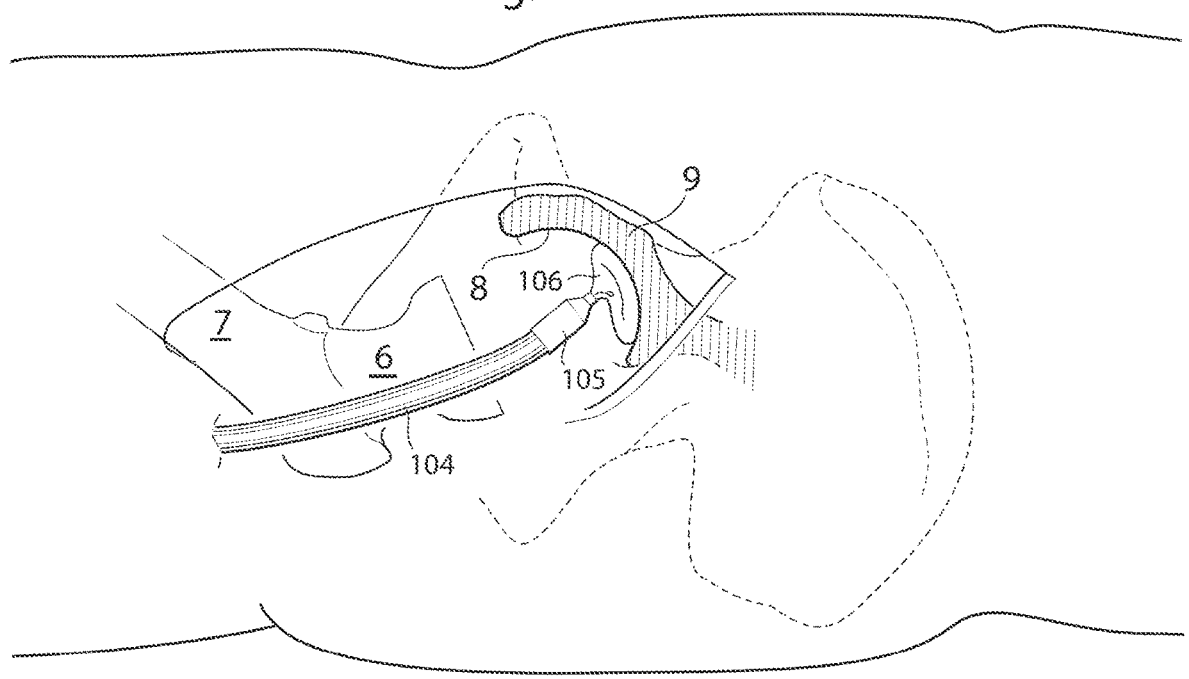
FIG. 14 shows the hip joint in section when a medical device for creating a hole in the pelvic bone is operating.

FIG. 14 shows the injection of an adhesive 106 in the acetabulum 8 in the pelvic bone 9 using an injecting member comprising an injecting nozzle 105, which is a preparation for the fixation of a medical device to the pelvic bone 9.

Figure 15:
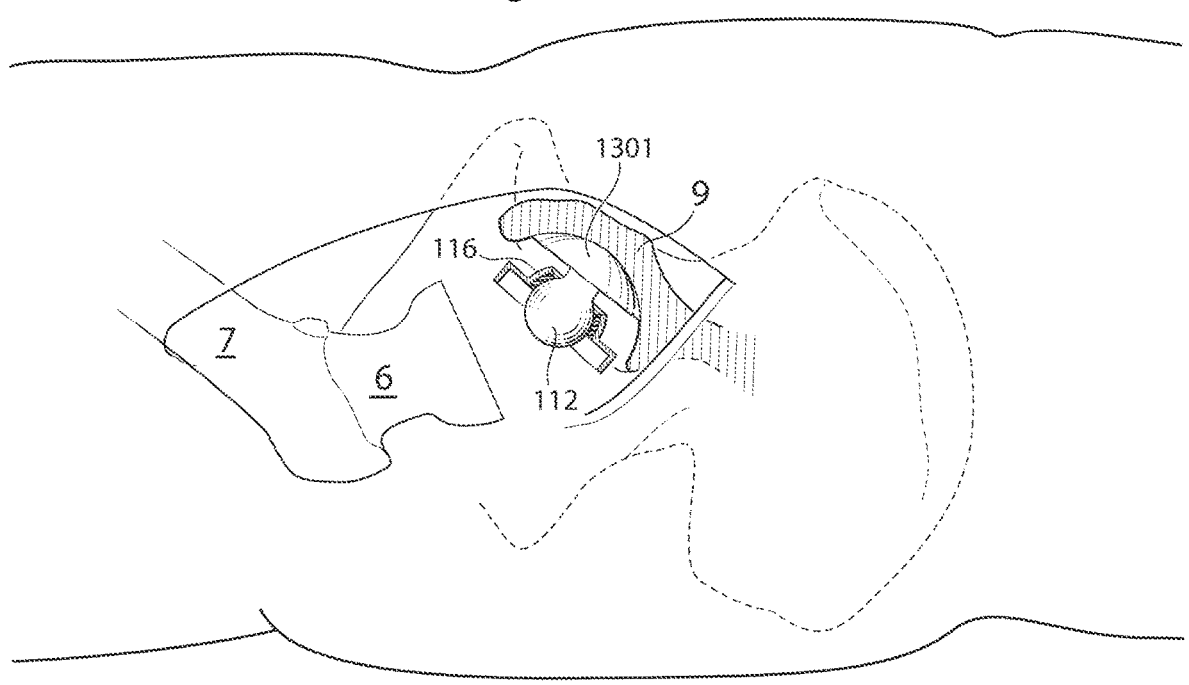
FIG. 15 shows the step of removing a proximal part of the caput femur.

FIG. 15 shows the placing of a medical device in the reamed acetabulum 8 surface of the pelvic bone 9. The medical device comprises a convex hip joint surface 112 fixated to a fixation element 1301, which in turn is fixated to the acetabulum 8 using the injected fluid, which could be assisted or replaced by a mechanical fixation element such as screws. The medical device further comprises a pre-mounted locking member 116 for locking the convex hip joint surface of the concave hip joint surface placed in the caput 5 and collum femur 6 for hindering dislocation of the hip joint when the hip joint is in its functional position.

Figure 16A:
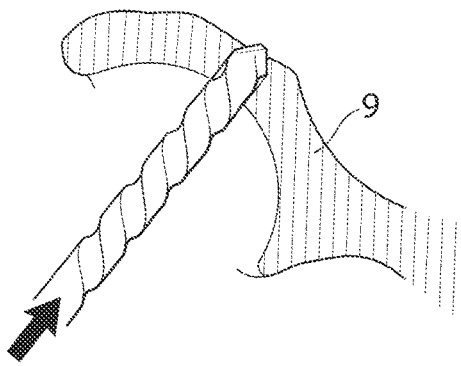
FIG. 16a-16i shows the hip joint in section when a reamer is introduced to a hole in the pelvic bone.

FIG. 16a shows the step of creating a hole in the pelvic bone 9 from the acetabulum side of the pelvic bone 9.

Figure 16B:
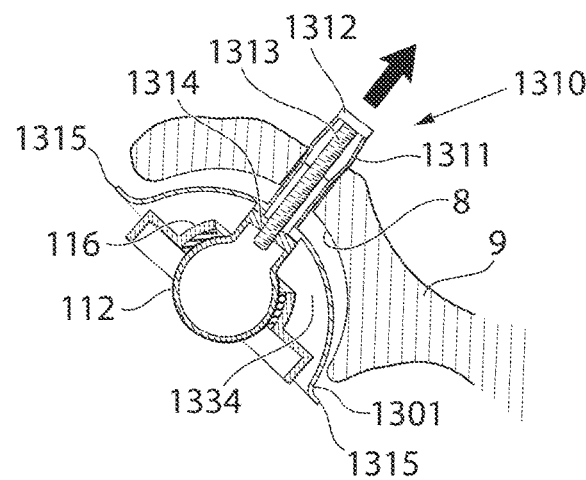

FIG. 16b shows the medical device according to an embodiment in which the medical device comprises a fixation element 1301 adapted to fixate the artificial convex caput femur 112 to the pelvic bone 9. The fixation element 1301 comprises a fixation surface 1334 which is adapted to fit into the acetabulum 8. The fixation surface 1334 could be adapted to be fixated against the acetabulum 8 using an adhesive, such as bone cement, applied to the fixation surface 1334 and/or the acetabulum surface 8. The medical device further comprises an elongated element 1310, here being an integrated part of the fixation element 1301. The elongated element 1310 is inserted through the hole in the pelvic bone 9, such that said elongated member 1310 is partially placed on the abdominal side of the pelvic bone 9. After insertion of the elongated member 1310, the elongated member 1310 is structurally changed on the abdominal side of the pelvic bone 9, such that said elongated member 1310 fixates the fixation element 1301 to the pelvic bone 9. According to the embodiment of FIG. 16b the elongated member 1310 comprises an expandable portion 1311, and the structural change comprises the expandable portion 1311 changing from a first, non-expanded state, in which the elongated element 1310 is inserted into the hole in the pelvic bone 9 substantially along a length axis of the elongated element 1310 into an expanded state, in which the expandable portion 1311 is expanded in at least one away from the length axis, such that said elongated element 1310 is placed in an expanded state, which fixates the fixation element 1301 to the pelvic bone 9. The expandable portion 1311 according to the embodiment shown in FIG. 16*b* comprises a plurality of expanding elements in connection with an anvil member 1312. A threaded member 1313 is placed centrally in the elongated element 1310 and is in one end connected to an anvil member 1312 and in the other end connected to a threaded portion 1314 of the artificial caput femur 112. By the connection with the threaded member 1313, the anvil member 1312 is adapted to press on the expanding elements following an action performed from the acetabulum side of the pelvic bone 9, such that said expanding elements expand in at least one direction substantially perpendicular to the length axis of the elongated element 1311. The fixation element shown in FIG. 16*b* further comprises a flange 1315 adapted to extend out of the acetabulum 8 and be placed in contact with the pelvic bone 9.

Figure 16C:
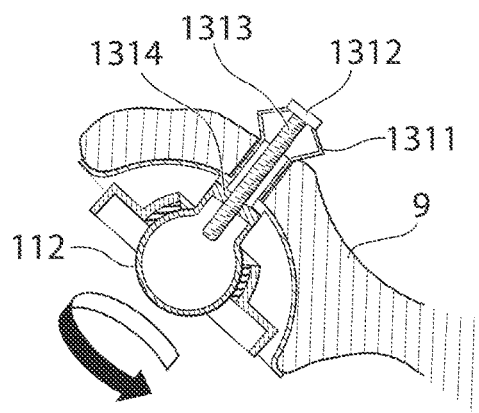

FIG. 16*c* shows the expandable portion 1311 when the anvil member 1312 has pressed the expandable elements in two directions perpendicular to the length axis of the elongated element 1310 for fixating the elongated element 1310 and the entire artificial caput femur 112 to the pelvic bone 9. The threaded part 1314, being a portion of the artificial caput femur 112, has been partially inserted into the artificial caput femur 112, and thus the anvil member 1312 is pulled towards the hole in the pelvic bone 9.

Figure 16D:
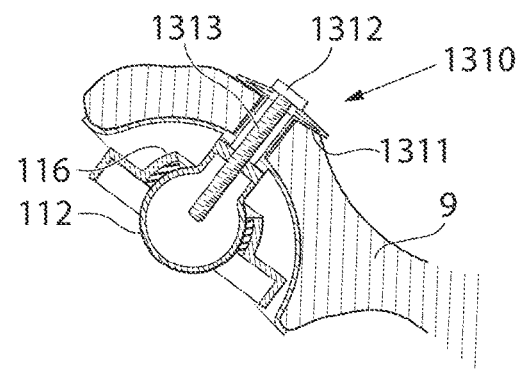

FIG. 16*d* shows the elongated member 1311 in the wholly expanded state fixating the artificial caput femur 112 to the pelvic bone 9. In this state the threaded member 1313 is positioned further into the artificial caput femur 112 which is rotated to tighten the expandable elongated element 1310. The locking member 116 is according to this embodiment pre-mounted onto the artificial caput femur 112 when the artificial caput femur 112 is implanted, however, according to other embodiments it is equally conceivable that the locking member 116 is adapted to be mounted after the artificial caput femur 112 has been implanted in the hip joint.

Figure 16E:
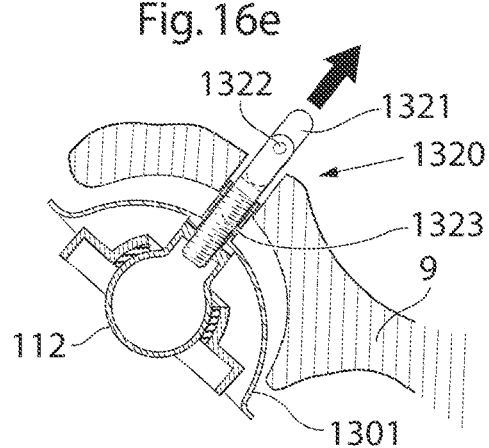

FIG. 16*e* shows the medical device according to an embodiment in which the implantable medical device comprises an elongated element 1320 comprising a movable locking portion 1321 adapted to have a first and second state, wherein said movable locking portion 1321, in said first state is adapted to be inserted into a hole in the pelvic bone 9, and in said second state is adapted to hinder the elongated element 1320 from passing through said hole in the pelvic bone 9 by said movable locking portion 1321 contacting the surface of the pelvic bone 9 on the abdominal side. FIG. 8*f* shows the elongated element 1320 in its first state after having passed through the hole in the pelvic bone 9.

Figure 16F:
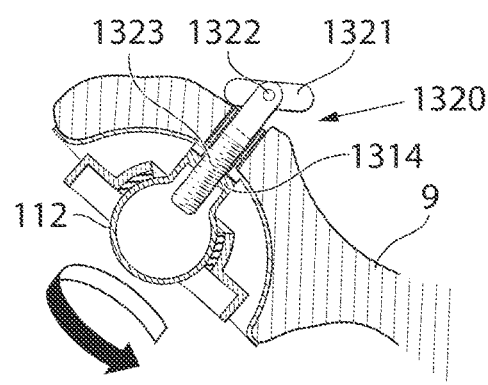

FIG. 16*f* shows the movable locking portion 1321 changing from the first to the second state at the same time as the artificial caput femur 112, comprising a threaded part 1314, interacts with a corresponding threaded member 1323 being part of the elongated element 1320. The movable locking portion 1321 is pivotally arranged at a pivot point 1322 and changes from the first to the second state using the pivot point 1322.

Figure 16G:
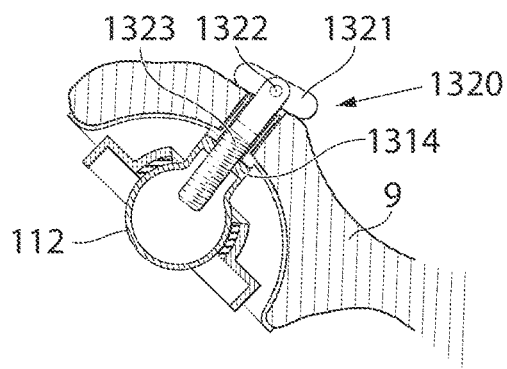

FIG. 16*g* shows the medical device according to the embodiment of FIGS. 16*e* and 16*f* when the movable member 1321 is placed in the second state, in which the artificial caput femur 112 is fixated to the pelvic bone 9 by the movable member 1321 being in contact with the abdominal side of the pelvic bone 9. The artificial caput femur 112 has been tightened using the threaded part 1314 and corresponding threaded member 1323, such that the entire medical device comprising the artificial caput femur 112 is securely fixated to the pelvic bone 9. Similar to the embodiments shown with reference to FIGS. 16*b*-16*d* the fixation element 1301 could be further fixated to the acetabulum 8 using an adhesive, such as bone cement, applied to the fixation surface and/or the acetabulum surface 8.

Figure 16H:
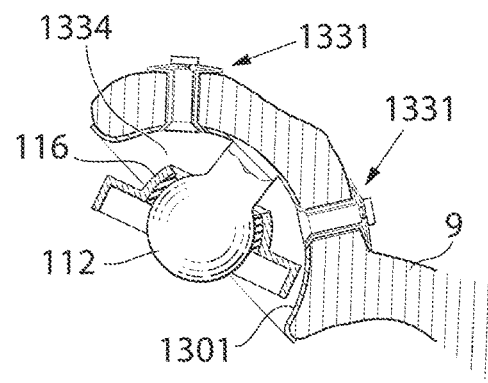

FIG. 16*h* shows an embodiment in which the fixation element comprises a fixation surface 1334 comprising two holes adapted to receive two mechanical fixation elements 1331. In the embodiment of FIG. 8*i* the mechanical fixation elements 1331 are expanding fixation elements 1331, such as the expanding fixation elements described with reference to FIGS. 16*b*-16*d*, however in other embodiments it is equally conceivable that the mechanical fixation elements are elements adapted to fixate the medical device to the internal periphery of the holes, such as screws. Similar to the embodiments shown with reference to FIGS. 16*b*-16*g* the fixation element 1301 could be further fixated to the acetabulum using an adhesive, such as bone cement, applied to the fixation surface and/or the acetabulum surface. FIG. 16*h* shows an embodiment in which the medical device has a pre-mounted locking member 116, however, in other embodiments it is equally conceivable that the locking member 116 is adapted to be mounted after the artificial caput femur 112 has been implanted in the hip joint.

Figure 16I:
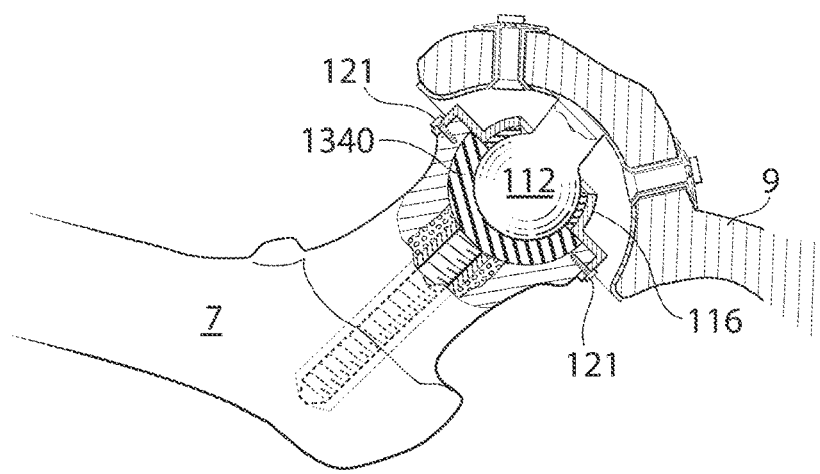

FIG. 16*i* shows the artificial hip joint in section, when the medical device described with reference to FIG. 16*h* has been implanted. Furthermore an artificial acetabulum surface 1340 having a concave surface towards the center of the hip joint has been implanted. The artificial acetabulum surface 1340 has been fixated to the femoral bone 7, and placed in movable contact with the artificial caput femur surface 112, thus creating a functioning artificial hip joint. The locking member 116 has been fixated to the femoral bone 7, thus locking the artificial caput femur 112 in the artificial acetabulum surface 1340. The locking member 116 is according to the embodiment shown in FIG. 8*j* fixated using screws 121, however the screws 121 could be assisted or replaced by an adhesive, such as bone cement.

FIG. 17*a* shows an assembled artificial hip joint with an artificial caput femur surface 112 fixated to the pelvic bone 9 using two fixating members adapted to expand inside of the cortical bone of the pelvic bone 9. The fixating members comprises a screw 121 in connection with an anvil member 1312 affecting an expandable portion 1311 pressing the expandable members in two directions perpendicular to the length axis of the fixation members for fixating the artificial caput femur 112 to the pelvic bone 9. The artificial acetabulum 1340 is fixated to the femoral bone 7 using an elongated member 1310*b* placed in the cancellous bone and aligned with the caput and collum femur center axis. The elongated member comprises an expandable portion 1311*b* which is pressed by an anvil member 1312*b* connected to a threaded member 1313*b* pressing the expandable members 1311*b* in two directions perpendicular to the length axis of the elongated member 1310*b* for fixating the artificial acetabulum surface to the femoral bone 7.

FIG. 17*b* shows an embodiment similar to the embodiment shown in FIG. 17*a* with the difference that the artificial acetabulum surface is fixated using an elongated member 1310*c* which penetrates the cancellous bone of the collum femur and the cortical bone of the femoral bone in the area of the greater trochanter 1695. The elongated member comprises a movable locking portion 1321*b*, pivotally arranged at a pivot point 1322*b*. The movable locking portion 1321*b* could change from a first to a second state around the pivot point 1322*b*. When the movable locking portion 1321*b* is placed in the second state it locks the elongated member on the outside of the femoral bone 7 in the area of the greater trochanter 1695.

FIG. 17*c* shows an embodiment similar to the embodiment shown in FIG. 17*a* with the difference that the artificial acetabulum surface is fixated using an elongated member 1310*d* which penetrates the cancellous bone of the collum femur and enters the cortical bone of the femoral bone in the area of the greater trochanter 1695 but never exits the bone but rather is fixated inside of the bone 7.

Figure 18A:
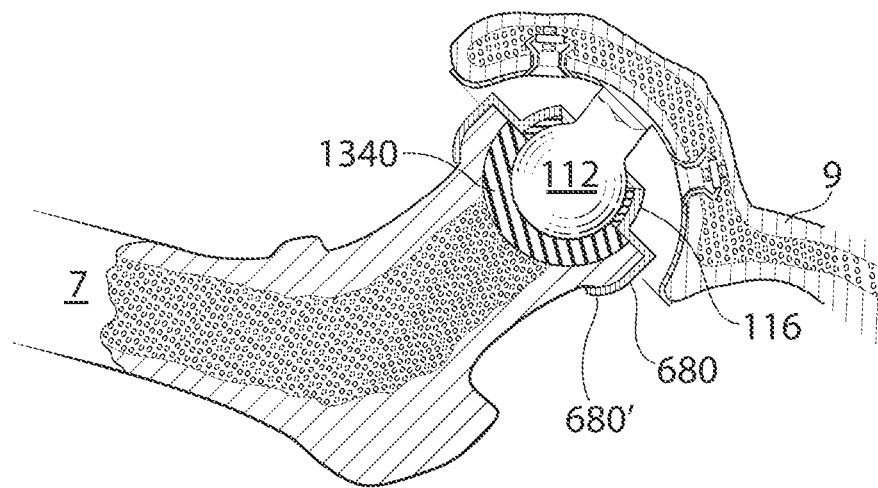
FIGS. 18a-18b shows the step of providing a medical device through a hole in the pelvic bone.

FIG. 18*a* shows an embodiment where the artificial acetabulum 1340 is fixated to the femoral bone 7 using fixating portions 680 being part of the locking member 116. The fixating portions 680 comprises portions 680' clasping the surgically cut femoral bone and thereby fixating the artificial acetabulum surface to the femoral bone.

Figure 18B:
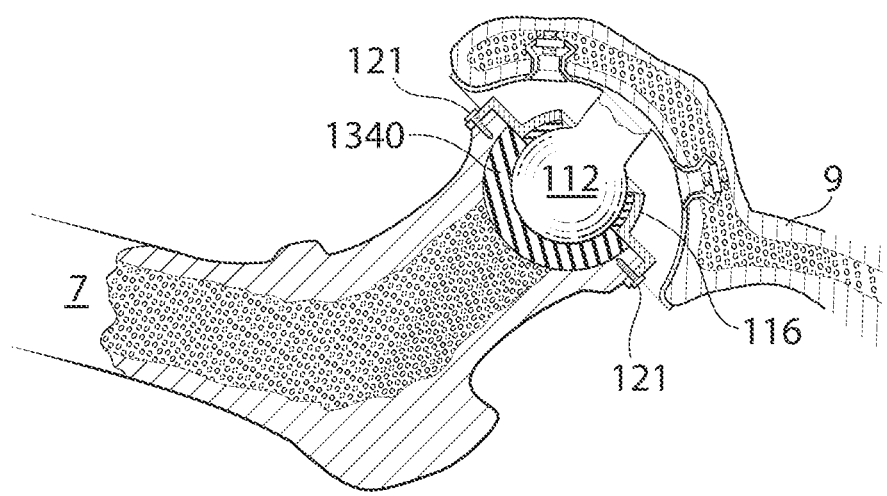

FIG. 18*b* shows an embodiment similar to the embodiment described with reference to FIG. 18*a* with the difference that the locking member is fixated to the surgically cut caput femur using screws 121.

Figure 19:
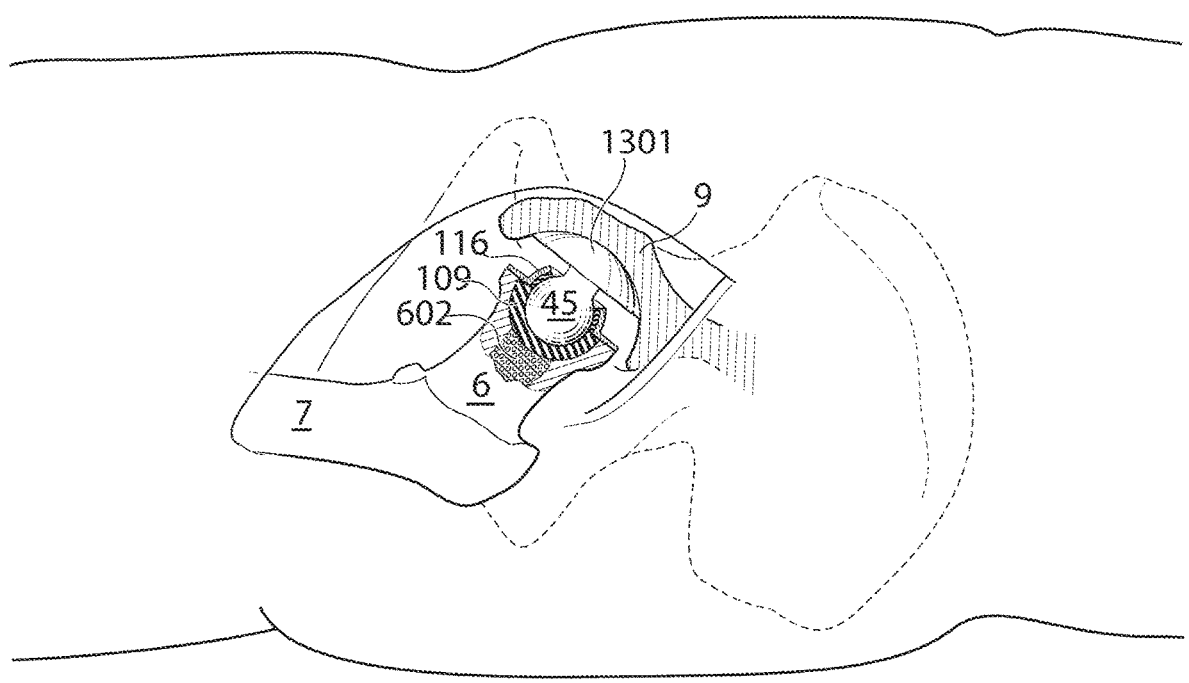
FIG. 19 shows the medical device in further detail.

FIG. 19 shows the hip joint in section when the medical device is assembled and in its functional position in the hip joint. The artificial caput femur surface 45 or convex hip joint surface 112 is fixated to the fixation part 1301, which in turn is fixated to the acetabulum 8, The locking member 116 locks the artificial convex caput femur surface 45 in the artificial concave acetabulum surface in the caput 5 and collum femur 6.

Figure 20:
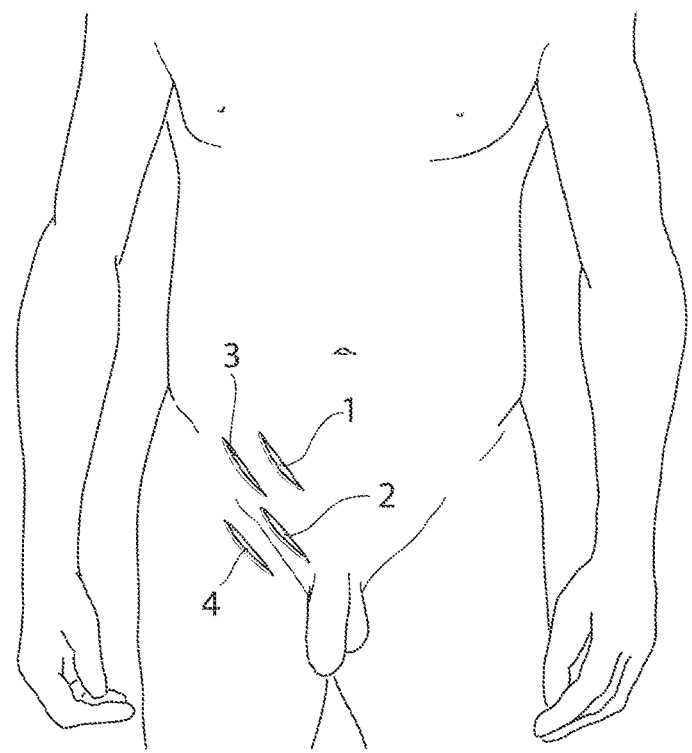
FIG. 20 shows the hip joint in section when a medical device has been provided.

FIG. 20 shows a frontal view of a human patient when an incision for reaching an area of the hip joint through the pelvic bone in a surgical method has been performed. According to one embodiment the incision 1 is made in the abdominal wall of the human patient. The incision 1 passes through the abdominal wall, preferably rectus abdominis and peritoneum, in to the abdomen of the human patent. In a second embodiment the incision 2 is conducted through the rectus abdominis and in to the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal channel. In all of the four embodiments the tissue surrounding the pelvic bone 9 in the area opposite to acetabulum is removed or penetrated which enables the surgeon to reach the pelvic bone 9. It is obvious that the methods described may both be combined or altered reaching the same goal to dissect the pelvic bone on the opposite side of the acetabulum.

Figure 21:
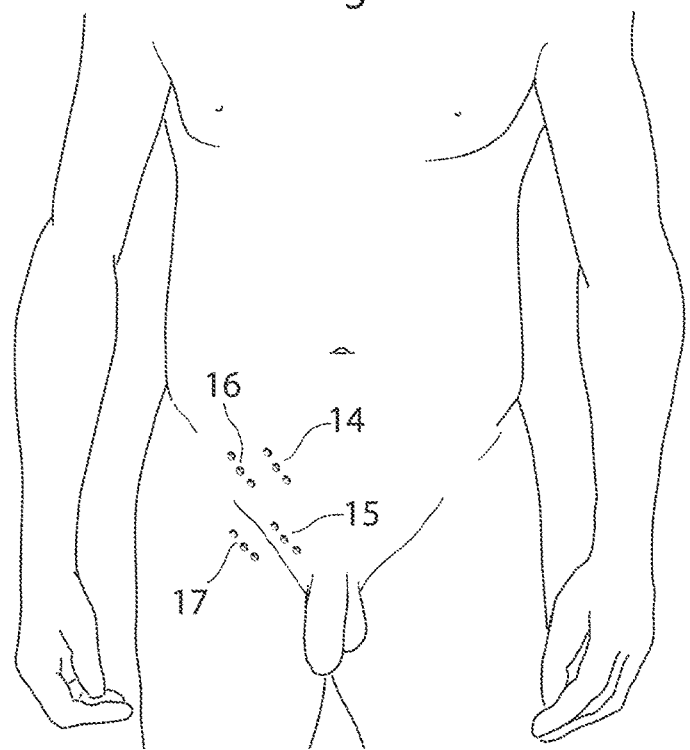
FIG. 21 shows the hip joint in section when a prosthetic part is being provided.

FIG. 21 shows a frontal view of a human patient when small incisions for reaching an area of the hip joint through the pelvic bone in a arthroscopic method has been performed. According to a first embodiment the incisions 14 is made in the abdominal wall of the human patient. The small incisions enable the surgeon to insert arthroscopic trocars into the abdomen of the human patient. According to the first embodiment the incisions 14 passes through the abdomen, preferably rectus abdominis and peritoneum, in to the abdomen of the human patent. According to a second embodiment the small incisions 15 is conducted through the rectus abdominis and in to the pelvic area, below peritoneum. According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

Figure 22:
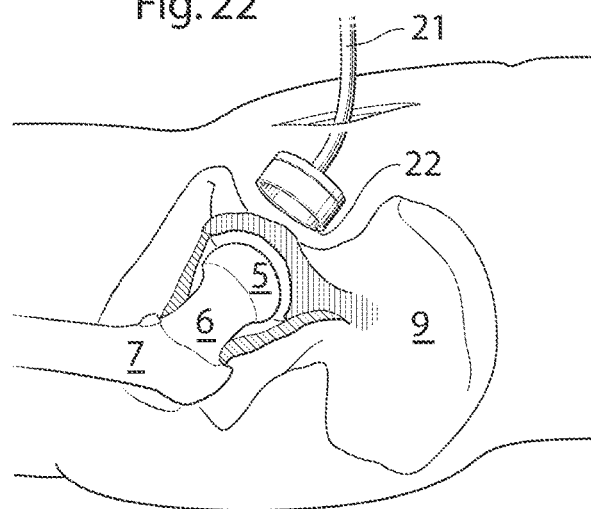
FIG. 22 shows the hip joint in section when the medical device has been fixated.

FIG. 22 shows the human patient in section when a medical device for creating a hole 18 in the pelvic bone 9 is inserted through an incision according to any of the embodiments described above. An elongated member 21, which could comprise a part or section adapted to be bent transfers force from an operating device (not shown) to the bone contacting organ 22. The bone contacting organ 22 is placed in contact with the pelvic bone 9 and creates a hole through a drilling, sawing or milling process powered by a rotating, vibrating or oscillating force distributed from the elongated member 21.

Figure 23:
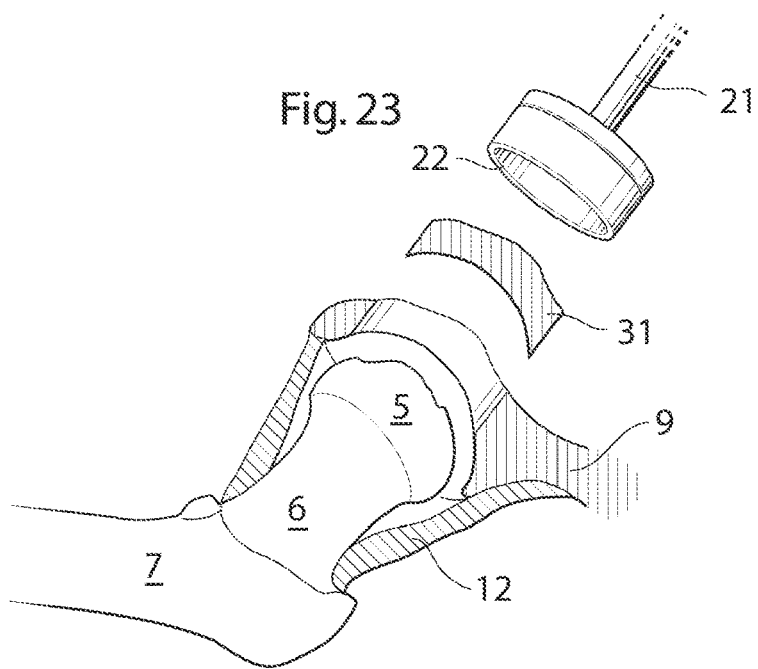
FIG. 23 shows a second approach to reaming the caput femur.

FIG. 23 shows the hip joint in section after the medical device for creating a hole 18 in the pelvic bone 9 has created said hole 18. According to this embodiment the hole 18 is created through the removal of a bone plug 31, however it is equally conceivable that said medical device comprises a bone contacting organ 22 adapted to create small pieces of bone, in which case the medical device could further comprise a system for transport of said small pieces of bone.

Figure 24:
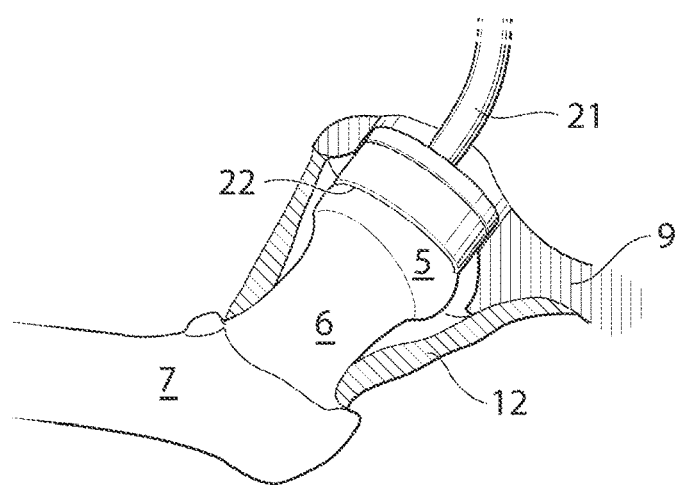
FIG. 24 shows the hip joint in section when an injecting member injects a fluid through a hole in the pelvic bone.

FIG. 24 shows how the medical device adapted to create a hole is inserted into the hip joint and placed in contact with the caput femur 5. According to this embodiment the medical device for creating a hole in the pelvic bone 9 and surgically cutting the caput femur 5 is the same medical device, however it is equally conceivable that there is a second medical device particularly adapted to surgically cut the caput femur 5.

Figure 25:
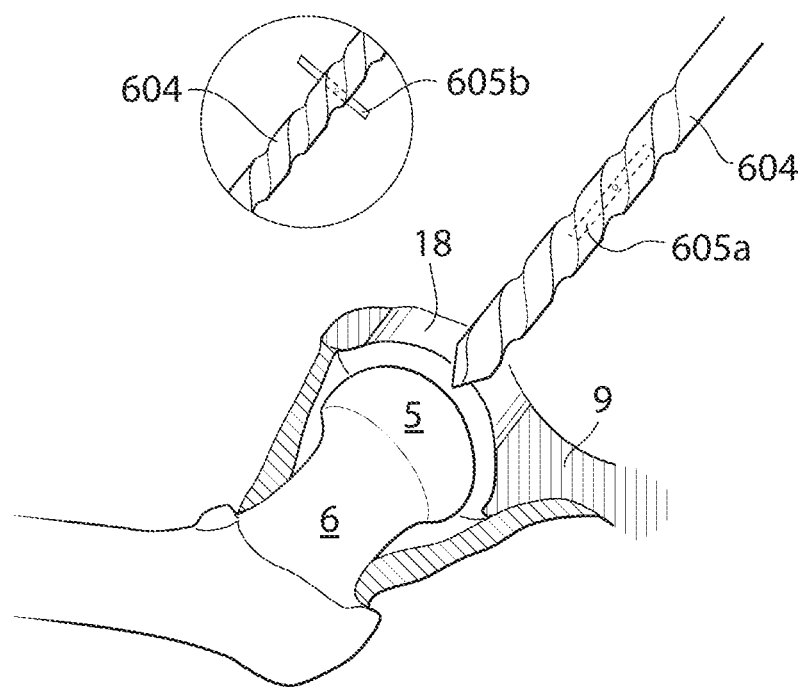
FIG. 25 shows a second approach to placing the medical device in the hip joint.

FIG. 25 shows the hip joint in section when a second medical device 604 surgically removes the most proximal portion of the caput femur 5. The second medical device 604 comprises a drilling portion in which a cutting member in a folded position 605*a* is placed.

Figure 26:
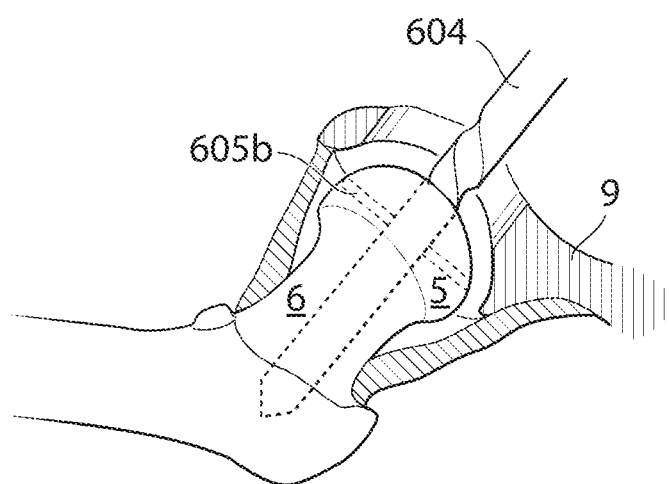
FIG. 26 shows a second approach to placing the medical device in the hip joint.

FIG. 26 shows the second medical device 604 when the drilling portion is positioned inside of the femoral bone, and the cutting member is placed in a cutting position 605*b* for cutting the proximal portion of the caput femur 5.

Figure 27:
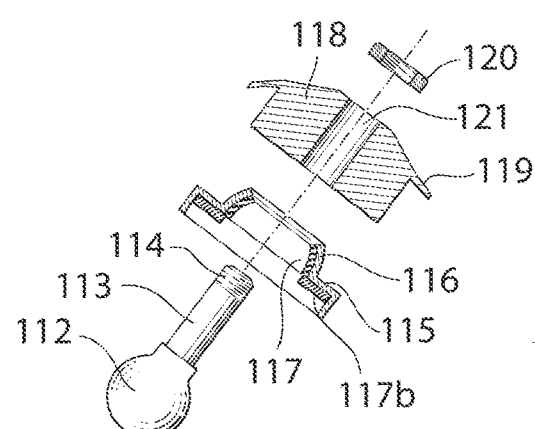
FIG. 27 shows the hip joint in section when a prosthetic part is being provided in a second approach.

FIG. 27 shows a medical device comprising an artificial convex hip joint surface 112. The artificial convex hip joint surface 112 is adapted to be fixated to the pelvic bone 9, and is adapted to be inserted through a hole 18 in the pelvic bone 9. The medical device comprises a nut 120, comprising threads for securely fixating the medical device to the pelvic bone 9. The medical device further comprises a prosthetic part 118 adapted to occupy the hole 18 created in the pelvic bone 9 after the medical device has been implanted in the patient. The prosthetic part 118 comprises supporting members 119 adapted to be in contact with the pelvic bone 9 and assist in the carrying of the load placed on the medical device from the weight of the human patient in normal use. Normal use is defined as the same as a person would use a natural hip joint. Further the medical device comprises a locking member 116 comprising a surface 117 adapted to be in contact with the artificial convex hip joint surface 112. The locking member 116 further comprises fixating members 115 which are adapted to assist in the fixation of the locking member 116 to the caput femur 5 or collum femur 6, which in turns fixates the artificial convex hip joint surface 112. The artificial convex hip joint surface 112 is fixated to an attachment rod 113 comprising a thread 114 that corresponds to the thread of the nut 120 in connection with the prosthetic part 118.

Figure 28:
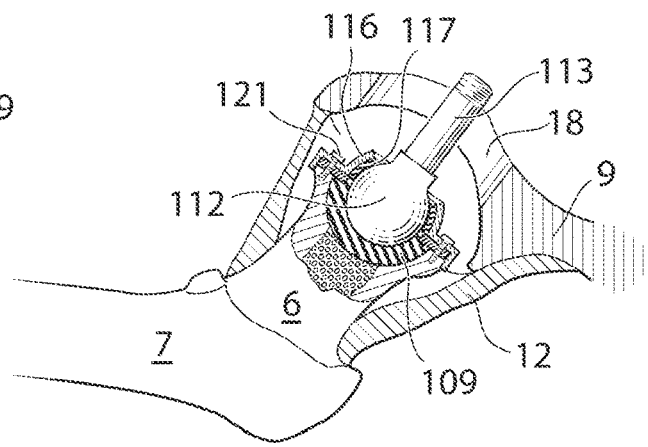
FIG. 28 shows the hip joint in section when the medical device has been fixated.

FIG. 28 shows the hip joint in section when the artificial convex hip joint surface is fixated in the medical device 109 comprising a concave hip joint surface 110. The convex hip joint surface 112 is secured in place by the locking member 116 which is fixated to the caput femur using screws 121. The surface of the locking member 117 and the concave hip joint surface 117 is placed in connection with the convex hip joint surface and could be made of a friction reducing material such as PTFE or a self lubricating powder material. However it is also conceivable that the connecting surfaces are lubricated using an implantable lubrication system adapted to lubricate the medical device after said medical device has been implanted in the human patient.

Figure 29:
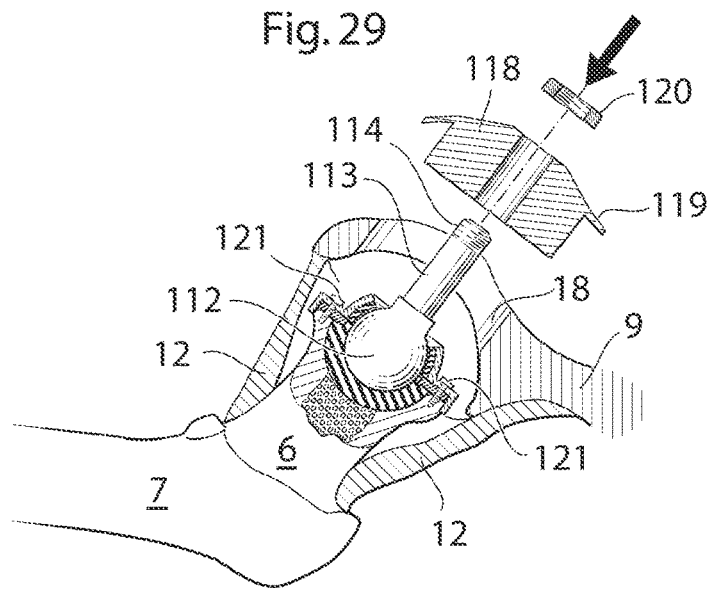
FIG. 29 shows a schematic view of the concave hip joint surface in section.

FIG. 29 shows the placing of a prosthetic part 118 adapted to occupy the hole 18 created in the pelvic bone 9. The prosthetic part 118 comprises supporting members 119 adapted to be in contact with the pelvic bone 9 and assist in the carrying of the load placed on the medical device from the weight of the human patient. According to the embodiment shown in FIG. 12 the supporting members 119 are located on the abdominal side of the pelvic bone 9, however it is equally conceivable the supporting members 119 are located on the acetabulum side of the pelvic bone 9, in which case they are preferably displaceable for allowing insertion of the prosthetic part 118 through the hole 18 in the pelvic bone 9. Furthermore FIG. 12 shows the fixation of a nut 120 to the attachment rod 113. According to the embodiment shown in FIG. 12 the hole 18 in the pelvic bone 9 is adapted to be larger than the medical device allowing the medical device to be inserted in its full functional size. According to other embodiments the hole 18 is smaller in which case the medical device could comprise of several parts adapted to be connected after insertion in the hip joint, or the medical device could be expandable for insertion through a hole smaller than the full functional size of the medical device. The expandable medical device could be enabled through the elements of the medical device comprising elastic material.

Figure 30:
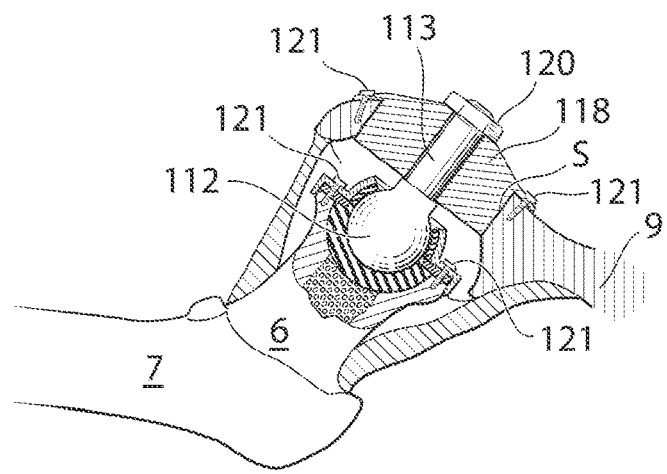
FIG. 30 shows an artificial concave acetabulum surface in section.

FIG. 30 shows the hip joint in section when all the elements of the medical device has been fixated in the area of the hip joint or its surroundings. The prosthetic part 113 adapted to occupy the hole 18 in the pelvic bone 9 is here fixated with screws 121, however these screws 121 could be assisted or replaced by an adhesive which could be applied to the surface S between the prosthetic part and the pelvic bone 9.

Figure 31:
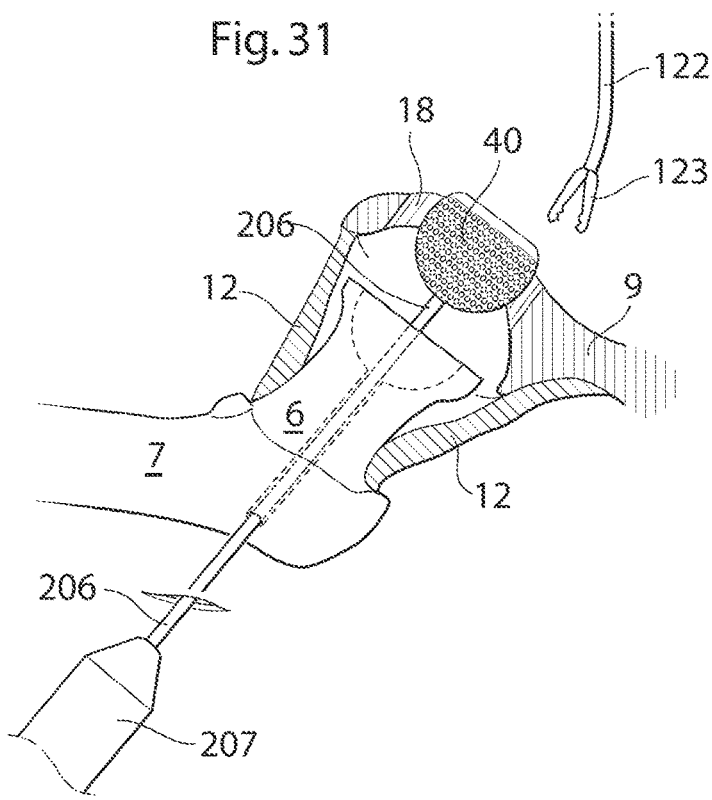
FIG. 31 shows the step of injecting a fluid into an area of the hip joint or its surroundings.

FIG. 31 shows the hip joint in section when the method of supplying the medical device is conducted according to another embodiment. The proximal part of the caput femur has been removed along the section created by the medical device for creating a hole. A reaming member 40 adapted to create a concave surface 103 in the caput femur 5 is here applied to a elongated member 206 which is inserted through a hole 205 going from the lateral side of the thigh, penetrating the cortical bone of the femoral bone 7 propagating along a length axis of the collum femur in the cancellous bone and entering the area of the hip joint. The elongated member 206 is operated using an operating device 207 which could be an electrically powered operating device, a hydraulically powered operating device or a pneumatically powered operating device. The reaming in the caput femur and part of the collum femur 6 is mainly performed in the cancellous bone, however that does not exclude the possibility the some of the reaming needs to be performed in the cortical bone of the caput femur 5 or the collum femur 6.

Figure 32:
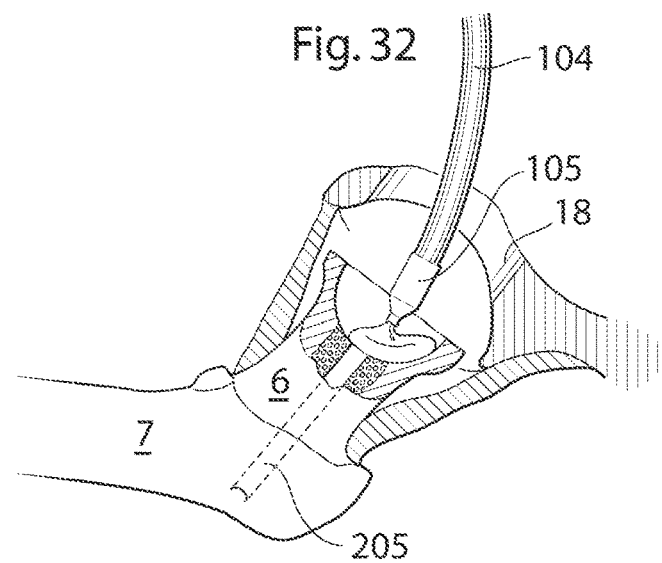
FIG. 32 shows the step of applying an adhesive 106 to the concave surface created by a reamer.

FIG. 32 shows the step of applying an adhesive 106 to the concave surface created by the reamer 40. The adhesive 106 is applied by an injecting member 104 comprising an injecting nozzle 105. The adhesive 106 is preferably a biocompatible adhesive such as bone cement. The injecting member 104 is in this embodiment adapted for introduction through a hole 18 in the pelvic bone 9, through the injecting member 104 being bent.

Figure 33:
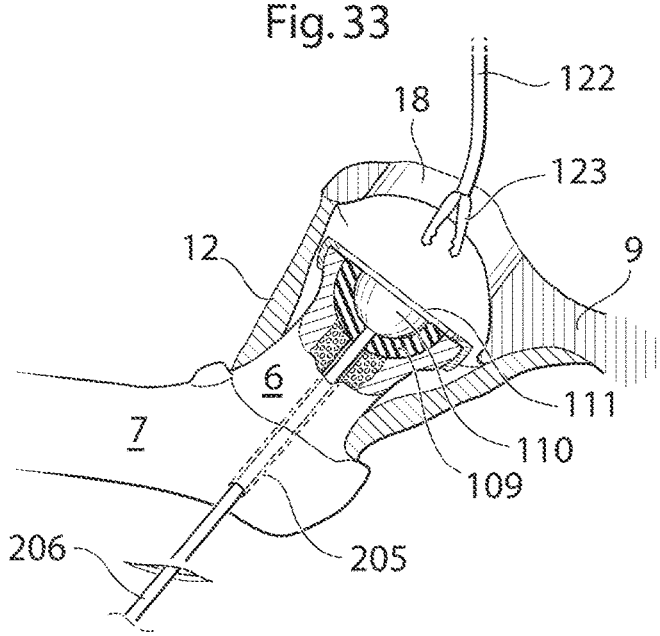
FIG. 33 shows the step of providing a medical device comprising an artificial concave hip joint surface.

FIG. 33 shows the step of providing a medical device 109 comprising an artificial concave hip joint surface 110. The medical device is according to this embodiment provided with a hole positioned in the length axis of the collum femur 6. The medical device is through the hole adapted to be guided by the elongated member 206 or a guiding rod placed in the hole 205 along a length axis of the collum femur 6. Inserting the medical device into the hip joint while the elongated member 206 or guiding rod runs through the hole of the medical device facilitates the positioning of the medical device and ensures the different parts of the medical device is centered for functioning as a unit. In the embodiment shown in FIG. 33 the medical device 109 is inserted into the hip joint as a single unit, however it is equally conceivable that the medical device 109 is inserted in parts (not shown) which are then connected to form the medical device after implantation in the patient. The artificial concave hip joint surface 110 is fixated to the concave surface 103 created in the caput femur 5 and collum femur 6. The medical device 109 comprises a fixation support 111 adapted to anchor said artificial concave hip joint surface 110, to at least one of the caput femur 5 and the collum femur 6. The medical device 109 is adapted to be introduced to the hip joint through a hole 18 in the pelvic bone 9 using a manipulation device 122 comprising a gripping member 123. According to this embodiment the manipulation device 122 is bent and thereby adapted to operate through a hole 18 in the pelvic bone 9. According to one embodiment the medical device 109 comprises a self lubricating material such as PTFE, however it is also conceivable that said medical device comprises: titanium, stainless steel, Corian, PE, or other acrylic polymers, in which case the medical device could be adapted to be lubricated after insertion in the hip joint.

Figure 34:
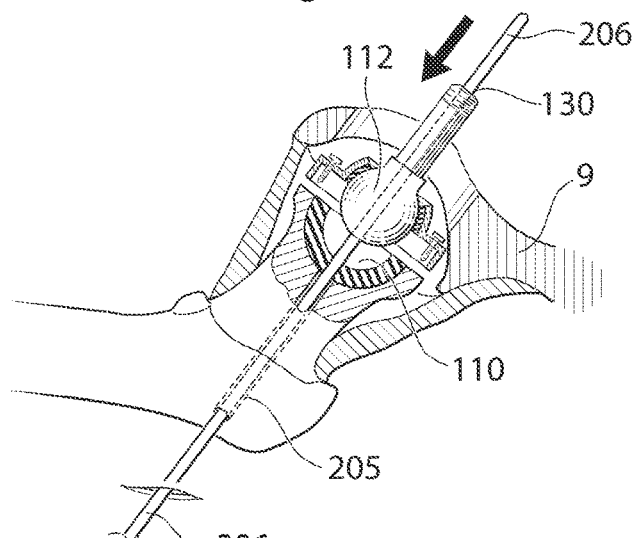
FIG. 34 shows the hip joint in section when the artificial convex hip joint surface is fixated in the medical device.

FIG. 34 shows the hip joint in section when the artificial convex hip joint surface is fixated in the medical device 109 comprising a concave hip joint surface 110, the medical device is guided using the elongated member 206 or a guiding rod. The convex hip joint surface 112 is secured in place by the locking member 116 which is fixated to the caput femur using screws 121, the convex hip joint surface is guided using the elongated member 206 or a guiding rod. The surface of the locking member 117 and the concave hip joint surface 110 is placed in connection with the convex hip joint surface and could be made of a friction reducing material such as PTFE or a self lubricating powder material. However it is also conceivable that the connecting surfaces are lubricated using an implantable lubrication system adapted to lubricate the medical device after said medical device has been implanted in the human patient. The elongated member or guiding rod 206 can be adapted to act as a centering rod for centering the at least one artificial hip joint surface inside of the hip joint. According to the embodiment shown the elongated member 206 is inserted through the femoral bone, however according to other embodiments, not shown, the elongated member is positioned inside of the hip joint from the acetabulum side.

Figure 35:
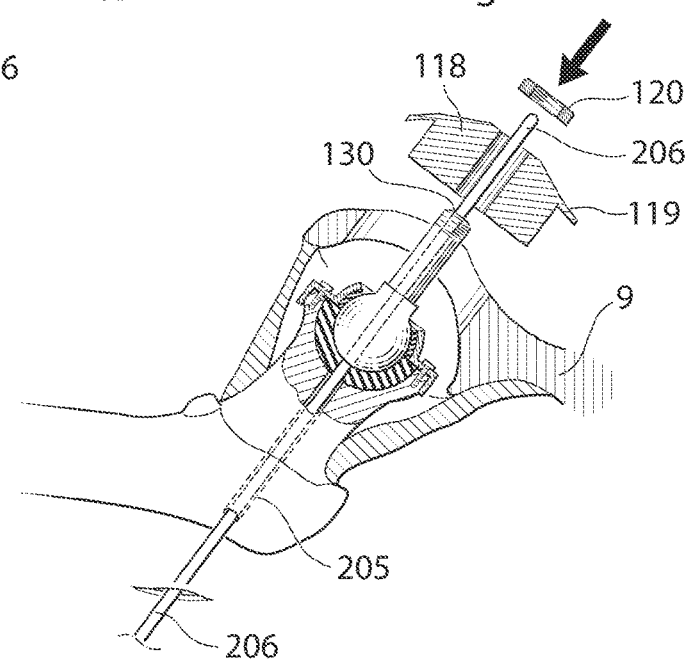
FIG. 35 shows the placing of a prosthetic part adapted to occupy the hole created in the pelvic bone.

FIG. 35 shows the placing of a prosthetic part 118 adapted to occupy the hole 18 created in the pelvic bone 9. The prosthetic part 118 comprises supporting members 119 adapted to be in contact with the pelvic bone 9 and assist in the carrying of the load placed on the medical device from the weight of the human patient. Furthermore FIG. 35 shows the fixation of a nut 120 to the attachment rod 113, which in turn is guided by the elongated member 206 or a guiding rod.

Figure 36:
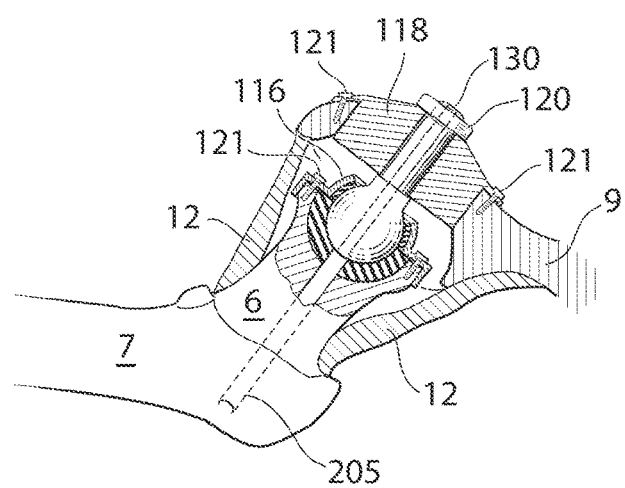
FIG. 36 shows the hip joint in section when all the elements of the medical device has been fixated in the area of the hip joint or its surroundings.

FIG. 36 shows the hip joint in section when all the elements of the medical device has been fixated in the area of the hip joint or its surroundings. The prosthetic part 118 adapted to occupy the hole 18 in the pelvic bone 9 is here fixated with screws 121, however these screws 121 could be assisted or replaced by an adhesive which could be applied to the surface S between the prosthetic part and the pelvic bone 9. The elongated member 206 or guiding rod has been retracted through the incision in the thigh.

FIG. 37 shows an embodiment of a locking member 116, wherein the locking member 116 comprises a surface adapted to be in contact with the artificial convex hip joint surface 1353, the locking member 116 is adapted to, in a first state, lock the artificial caput femur 112 to the artificial acetabulum surface 1340, and in a second state, release said artificial caput femur 112 from said artificial acetabulum 1340. The locking member 116 is adapted to change from the first to the second state when a predetermined amount of strain is placed on the locking member 116. The locking member 116 according to the embodiment shown in FIG. 37, comprises four elastic portions 1351, and the locking member 116 is adapted to change from the first to the second state using the elasticity of the elastic portions 1351. The locking member 116 is adapted to be fixated to the femoral bone 7 using screws adapted to be placed in holes 1352 adapted therefor.

FIG. 38 shows the hip joint in section when a two state locking member 116 locks the artificial caput femur 112 in the artificial acetabulum 1340. The two state locking member 116 is fixated to the femoral bone 7 using screws 121, and is here shown in its first state in which the locking member 116 locks the artificial caput femur 112 to the artificial acetabulum 1340.

FIG. 39 shows the hip joint in section according to the embodiment of FIG. 38, but when the two state locking member 116 is in its second state, in which the locking ring 116 releases the artificial caput femur 112 from the artificial acetabulum surface 1340. The construction with the releasing locking ring 116 reduces the risk of strain placed on the artificial joint injuring the fixation points, i.e. the contact with bone; it further enables the artificial joint to be non-invasively relocated in case of luxation.

According to the above mentioned embodiments the medical device is adapted to be inserted through a hole in the pelvic bone, however it is equally conceivable that the medical device according to any of the embodiment above is adapted to be inserted through a hole in the hip joint capsule or the femoral bone of the human patient.

Please note that any embodiment or part of embodiment as well as any method or part of method could be combined in any way. All examples herein should be seen as part of the general description and therefore possible to combine in any way in general terms.

The invention claimed is:

1. A medical device for implantation in a hip joint of a human patient, the hip joint having a ball shaped caput femur as a proximal part of a femoral bone with a convex hip joint surface towards a centre of the hip joint and an acetabulum as part of a pelvic bone with a concave hip joint surface towards the centre of the hip joint, the medical device comprising; an artificial caput femur, comprising a convex surface towards the centre of the hip joint, wherein said artificial caput femur is adapted to, when implanted:
   a. be fixated to the pelvic bone of the human patient, and
   b. be in movable connection with an artificial acetabulum surface fixated to the femoral bone of the patient, thereby forming a ball and socket joint, wherein
   the medical device further comprises a fixation element comprising a fixation surface adapted to be in contact with a surface of the acetabulum or its surroundings and adapted to fixate the artificial caput femur to at least acetabulum of the pelvic bone, such that there is a gap at least a portion of the artifical caput femur and the acetabulum.

2. The medical device according to claim 1, wherein said fixation element is at least one of:
   a. comprising at least one hole adapted to receive a mechanical fixation element, or
   b. adapted to fixate to the pelvic bone using an adhesive placed between said fixation surface and said surface of the acetabulum, when said medical device is implanted in the hip joint.

3. The medical device according to claim 1, wherein further comprising an elongated member is adapted to:
   a. be inserted through a hole in the pelvic bone, such that said elongated member is partially placed at least one of:
      i. inside of the pelvic bone, or
      ii. on an abdominal side of the pelvic bone opposite the acetabulum, and
   b. adapted to be structurally changed inside of the pelvic bone or on the abdominal side of the pelvic bone, such that said elongated member fixates the fixation element to the pelvic bone and at least a portion of said elongated member contacts the pelvic bone on the inside or abdominal side thereof, when implanted.

4. The medical device according to claim 3, wherein said elongated member comprises an expandable portion, wherein said expandable portion is adapted to:
   a. in a first, non-expanded state, be inserted through the hole in the pelvic bone, substantially along a length axis of said elongated member,
   b. expand in a direction non-parallel relative to said length axis, such that said elongated member is placed in an expanded state, which fixates the fixation element to the pelvic bone, on the inside or abdominal side thereof.

5. The medical device according to claim 4, wherein said expandable portion comprises two or more expanding elements in connection with an anvil member, wherein said anvil member is adapted to press on the expanding elements following an action performed from the acetabulum side of the pelvic bone, such that said two or more expanding elements expands in at least one direction substantially perpendicular to the length axis of the elongated member.

6. The medical device according to claim 5, wherein said anvil member is in connection with a threaded portion of the elongated member, the threaded portion extending substantially along the length axis of the elongated member, and wherein said artificial caput femur further comprises a threaded part with cooperating threads, such that rotating said artificial caput femur results in said threaded portion being pulled in the direction of the acetabulum side of the pelvic bone, which by the connection with the anvil member presses said two or more expanding elements.

7. The medical device according to claim 4, wherein said expandable portion of said elongated member is adapted to expand at least in one direction away from said length axis, when a rotational movement is performed from the acetabulum side of the pelvic bone, when said device is implanted.

8. The medical device according to claim 3, wherein said elongated member comprises a movable locking portion adapted to have a first and second state, wherein said movable locking portion, in said first state is adapted to be inserted into a hole in the pelvic bone, and in said second state is adapted to hinder the elongated member from passing through said hole in the pelvic bone by said movable locking portion contacting the surface of the pelvic bone on the abdominal side thereof.

9. The medical device according to claim 8, wherein said movable locking portion is pivotally arranged to said elongated member.

10. The medical device according to claim 1, wherein the artificial caput femur comprises a threaded part adapted to engage a corresponding threaded member, and wherein said artificial convex caput femur is adapted to be further fixated to the pelvic bone by a relative rotating movement of the artificial convex caput femur in relation to said threaded member.

11. The medical device according to claim 1, wherein said fixation element comprises at least one hole adapted to receive an an elongated member adapted to be placed in said hole, wherein said elongated member is further adapted to:
  a. be inserted through a hole in the pelvic bone, such that said elongated member is partially placed on the an abdominal side of the pelvic bone opposite the acetabulum, and
  b. be structurally changed on the abdominal side of the pelvic bone, such that said elongated member fixates the fixation element to the pelvic bone.

12. The medical device according to claim 1, further comprising said artificial acetabulum surface, comprising a concave surface towards the centre of the hip joint, adapted to, when implanted, be fixated to the femoral bone of the human patient, and be in movable connection with the convex surface of the artificial caput femur.

13. The medical device according to claim 12, wherein said medical device further comprises a second fixation element comprising a fixation surface adapted to be in contact with a surface of the caput femur or collum femur, wherein said second fixation element is adapted to fixate the concave surface of the artificial acetabulum to the femoral bone.

14. The medical device according to claim 12, further comprising an elongated member comprising an expandable portion adapted to:
  a. in a first, non-expanded state, be inserted through a hole in the femoral bone, substantially along a length axis of the elongated member, and
  b. expand at least in one direction away from said length axis, such that said elongated member is placed in an expanded state, which fixates the fixation element to the femoral bone, from the inside thereof.

15. The medical device according to claim 12, wherein said artificial acetabulum surface comprises at least one beyond part adapted to pass beyond the equator of the artificial caput femur, clasping said artificial caput femur for fixating said artificial caput femur in said artificial acetabulum surface.

16. A medical device for implantation in a hip joint of a human patient, the hip joint having a ball shaped caput femur as a proximal part of a femoral bone with a convex hip joint surface towards a central location of the hip joint between the caput femur and an acetabulum and a bowl shaped acetabulum as part of a pelvic bone with a concave hip joint surface, the medical device comprising; an artificial caput femur, comprising a convex surface, wherein said artificial caput femur is adapted to, when implanted,
  be immovably fixated to the pelvic bone of the human patient, and
  be in movable connection with an artificial acetabulum surface fixated to the femoral bone of the patient, thereby forming a ball and socket joint, wherein
the medical device further comprises a fixation element connected to said artificial caput femur and configured to be in contact with a surface opposite acetabulum on an abdominal side of the pelvic bone, for fixating the artificial caput femur to the pelvic bone.

17. The medical device according to claim 16, wherein said artificial acetabulum comprises a concave surface towards the center of rotation of the hip joint, adapted to, when implanted, be fixated to the femoral bone of the human patient, and be in movable connection with the convex surface of the artificial caput femure and wherein the medical device further comprises a fixating portion comprising a fixation surface adapted to be in contact with the caput femur or collum femur, wherein said fixating portion is adapted to fixate the artificial acetabulum to the femoral bone.

18. The medical device according to claim 16, wherein said fixation element comprises at least one hole adapted to receive a mechanical fixation element.

19. The medical device according to claim 16, wherein said fixation element further comprises a convex fixation surface adapted to be in contact with, and fixate to-a surface of the acetabulum and to fixate said medical device to the pelvic bone using an adhesive placed between said convex fixation surface and said surface of the acetabulum, when said device is implanted in the hip joint.

20. The medical device according to claim 16, wherein said fixation element comprises an elongated member, and wherein said elongated member is adapted to:
  a. be inserted through a hole in the pelvic bone, such that said elongated member is adapted to be partially placed at least one of:
    i. inside of the pelvic bone, or
    ii. on the abdominal side of the pelvic bone, and
  b. be structurally changed such that said elongated member is adapted to fixate the fixation element to the pelvic bone, and adapted to be contacting the pelvic bone on the inside thereof, when implanted.

* * * * *